(12) United States Patent
Hyde et al.

(10) Patent No.: US 9,649,425 B2
(45) Date of Patent: May 16, 2017

(54) DEVICE, SYSTEM, AND METHOD INCLUDING MICRO-PATTERNED CELL TREATMENT ARRAY

(71) Applicant: Searete LLC, Bellevue, WA (US)

(72) Inventors: Roderick A. Hyde, Redmond, WA (US); Lowell L. Wood, Jr., Bellevue, WA (US)

(73) Assignee: Gearbox, LLC, Bellevue, WA (US)

( * ) Notice: Subject to any disclaimer, the term of this patent is extended or adjusted under 35 U.S.C. 154(b) by 0 days.

(21) Appl. No.: 14/291,435

(22) Filed: May 30, 2014

(65) Prior Publication Data

US 2014/0276382 A1 Sep. 18, 2014

Related U.S. Application Data

(60) Division of application No. 13/200,496, filed on Sep. 23, 2011, now Pat. No. 8,747,347, which is a
(Continued)

(51) Int. Cl.
*G01N 33/50* (2006.01)
*A61M 1/36* (2006.01)
(Continued)

(52) U.S. Cl.
CPC ........... *A61M 1/3689* (2014.02); *B82Y 20/00* (2013.01); *G01N 33/5091* (2013.01); *C12Q 3/00* (2013.01); *Y10T 436/115831* (2015.01)

(58) Field of Classification Search
None
See application file for complete search history.

(56) References Cited

U.S. PATENT DOCUMENTS

| 6,228,326 B1 | 5/2001 | Boxer et al. |
| 6,503,452 B1 | 1/2003 | Boxer et al. |

(Continued)

FOREIGN PATENT DOCUMENTS

| WO | WO 01/20330 A1 | 3/2001 |
| WO | WO 01/88182 A2 | 11/2001 |

(Continued)

OTHER PUBLICATIONS

Andreasson-Ochsner, Mirjam et al.; "Single cell 3-D platform to study ligand mobility in cell-cell contact"; Lab on a Chip; Sep. 7, 2011; pp. 2876-2883; vol. 11, No. 17; The Royal Society of Chemistry.

(Continued)

*Primary Examiner* — Rebecca Martinez

(57) ABSTRACT

Devices, systems, or methods are disclosed herein for treatment of disease in a vertebrate subject. The device can include a quasi-planar substrate; and one or more laterally-mobile effector molecule types at least partially embedded within the quasi-planar substrate, wherein the one or more laterally-mobile effector molecule types is configured to interact with one or more cell types. The device can further include one or more sensors configured to detect at least one aspect of an interaction between the at least one of the one or more laterally-mobile effector molecule types and the one or more cell types; and a controller in communication with the one or more sensors, wherein the controller is configured to responsively initiate modification of at least one of the one or more laterally-mobile effector molecule types, the quasi-planar substrate, and the one or more cell types.

46 Claims, 2 Drawing Sheets

Related U.S. Application Data continuation of application No. 13/135,130, filed on Jun. 24, 2011, now Pat. No. 8,753,309.

(51) Int. Cl.
*B82Y 20/00* (2011.01)
*C12Q 3/00* (2006.01)

(56) References Cited

U.S. PATENT DOCUMENTS

| | | |
|---|---|---|
| 6,699,719 B2 | 3/2004 | Nguyen et al. |
| 7,141,656 B2 | 11/2006 | Rhode et al. |
| 7,435,578 B2 | 10/2008 | Wikswo et al. |
| 2002/0009807 A1 | 1/2002 | Kam et al. |
| 2004/0018601 A1 | 1/2004 | Boxer et al. |
| 2004/0121377 A1 | 6/2004 | Ishii et al. |
| 2004/0219523 A1 | 11/2004 | Stanton et al. |
| 2004/0219605 A1 | 11/2004 | Finkel et al. |
| 2005/0208120 A1 | 9/2005 | Albani |
| 2006/0110728 A1 | 5/2006 | Pompon et al. |
| 2008/0317724 A1 | 12/2008 | Kam et al. |
| 2009/0029874 A1 | 1/2009 | Lu et al. |
| 2010/0248284 A1 | 9/2010 | Chen et al. |

FOREIGN PATENT DOCUMENTS

| | | |
|---|---|---|
| WO | WO 02/12546 A2 | 2/2002 |
| WO | WO 2004/025262 A2 | 3/2004 |

OTHER PUBLICATIONS

European Patent Office, Supplementary European Search Report, Pursuant to Rule 62 EPC; App. No. EP 12803372; Nov. 6, 2014 (received by our Agent on Dec. 18, 2014); pp. 1-10.

Ali et al.; "In Situ Regulation of DC Subsets and T Cells Mediates Tumor Regression in Mice"; Sci Transl Med; Nov. 25, 2009; pp. 1-10; vol. 1, No. 8ra19; American Association for the Advancement of Science.

Angelot et al.; "Endothelial cell-derived microparticles induce plasmacytoid dendritic cell maturation: potential implications in inflammatory diseases"; Haematologica; 2009; pp. 1502-1512; vol. 94, No. 11; Ferrata Storti Foundation.

Bettelli et al.; "Reciprocal developmental pathways for the generation of pathogenic effector $T_H17$ and regulatory T cells"; Nature; May 11, 2006; pp. 235-238; vol. 441; Nature Publishing Group.

Bollyky et al.; "CD44 Costimulation Promotes FoxP3 + Regulatory T Cell Persistence and Function via Production of IL-2, IL-10, and TGF-$\beta^1$"; J. Immunol.; 2009; pp. 2232-2241; vol. 183; The American Association of Immunologists, Inc.

Choi et al.; "Hematopoietic and Endothelial Differentiation of Human Induced Pluripotent Stem Cells"; Stem Cells; 2009; pp. 559-567; vol. 27; AlphaMed Press.

Corsel et al.; "The Role of Intrinsic Binding Rate and Transport Rate in the Adsorption of Prothrombin, Albumin, and Fibrinogen to Phospholipid Bilayers"; Journal of Colloid and Interface Science; Jun. 1986; pp. 544-554; vol. 111, No. 2; Academic Press, Inc.

Cotner et al.; "Simultaneous Flow Cytometric Analysis of Human T Cell Activation Antigen Expression and DNA Content"; J. Exp. Med.; Feb. 1983; pp. 461-472; vol. 157; The Rockefeller University Press.

Cullen et al.; "Detection of Immunon-complex Formation via Surface Plasmon Resonance on Gold-coated Diffraction Gratings"; Biosensors; 1987/88; pp. 211-225; vol. 3; Elsevier Applied Science Publishers Ltd.

Doh et al.; "Immunological synapse arrays: Patterned protein surfaces that modulate immunological synapse structure formation in T cells"; PNAS; Apr. 11, 2006; pp. 5700-5705; vol. 103, No. 15; The National Academy of Sciences of the USA.

Enger et al.; "Optical tweezers applied to a microfluidic system"; Lab Chip; 2004; pp. 196-200; vol. 4; The Royal Society of Chemistry.

Gilboa, Eli; "DC-based cancer vaccines"; The Journal of Clinical Investigation; May 2007; pp. 1195-1203; vol. 117, No. 5.

Graf et al.; "Forcing cells to change lineages"; Nature; Dec. 3, 2009; pp. 587-594; vol. 462; Macmillan Publishers Limited.

Herrmann et al.; "Construction of Optimized Bispecific Antibodies for Selective Activation of the Death Receptor CD95"; Cancer Res; Feb. 15, 2008; pp. 1221-1227; vol. 68, No. 4; American Association for Cancer Research.

Hoffmann et al.; "Large-scale in vitro expansion of polyclonal human CD4+CD25$^{high}$ regulatory T cells"; Blood; Aug. 1, 2004; pp. 895-903; vol. 104, No. 3; The American Society of Hematology.

Holler et al.; "Two Adjacent Trimeric Fas Ligands Are Required for Fas Signaling and Formation of a Death-Inducing Signaling Complex"; Molecular and Cellular Biology; Feb. 2003; pp. 1428-1440; vol. 23, No. 4; American Society for Microbiology.

Krug et al.; "Toll-like receptor expresion reveals CpG DNA as a unique microbial stimulus for plasmacytoid dendritic cells with synergizes with CD40 ligand to induce high amounts of IL-12"; Eur. J. Immunol.; 2001; pp. 3026-3037; vol. 31; WILEY-VCH Verlag GmbH, D-69451 Weinheim.

Kohner et al.; "Lipid Mono- and Bilayer Supported on Polymer Films: Composite Polymer-Lipid Films on Solid Substrates"; Biophysical Journal; Jul. 1994; pp. 217-226; vol. 67; Biophysical Society.

Lai et al.; "Aptamer-Based Electrochemical Detection of Picomolar Platelet-Derived Growth Factor Directly in Blood Serum"; Anal. Chem.; 2007; pp. 229-233; vol. 79, No. 1; American Chemical Society.

Lee et al.; "Aptamers as molecular recognition elements for electrical nanobiosensors"; Anal Bioanal Chem; 2008; pp. 1023-1032; vol. 390; Springer-Verlag.

Liu et al.; "A facile 'liquid molding' method to fabricate PDMS microdevices with 3-dimensional channel topography"; Lab Chip; 2009; pp. 1200-1205; vol. 9; The Royal Society of Chemistry.

MacDonald et al.; "A simplified method for the preparation of detergent-free lipid rafts"; Journal of Lipid Research; 2005; pp. 1061-1067; vol. 46; American Society for Biochemistry and Molecular Biology, Inc.

MacDonald et al.; "Microfluidic sorting in an optical lattice"; Nature; Nov. 27, 2003; pp. 421-424; vol. 426; Nature Publishing Group.

Michnoff et al.; "Mutations within the $NH_2$-terminal Transmembrane Domain of Membrane Immunoglobulin (Ig) M Alters Ig$\alpha$ and Ig$\beta$ Association and Signal Transduction"; The Journal of Biological Chemistry; Sep. 30, 1994; pp. 24237-24244; vol. 269, No. 39; The American Society for Biochemistry and Molecular Biology, Inc.

Miltenyi Biotec; "Blood Dendritic Cell Isolation Kit II"; 2008; pp. 1-4; located at www.miltenyibiotec.com.

Nellen et al.; "Integrated Optical Input Grating Couplers as Chemo- and Immunosensors"; Sensors and Actuators; 1990; pp. 592-596; vol. B1; Elsevier Sequoia.

Neumann et al.; "Transport, Separation, and Accumulation of Proteins on Supported Lipid Bilayers"; Nano Lett.; 2010; pp. 2903-2908; vol. 10; American Chemical Society.

Pansri et al.; "A compact phage display human scFv library for selection of antibodies to a wide variety of antigens"; BMC Biotechnology; 2009; pp. 1-16; vol. 9, No. 6; BioMed Central Ltd.

PCT International Search Report; International App. No. PCT/US12/43560; Oct. 26, 2012; pp. 1-4.

Petersen, Kurt E.; "Silicon as a Mechanical Material"; Proceedings of the IEEE; May 1982; pp. 420-457; vol. 70, No. 5; IEEE.

"Quantification of Cell Adhesivity"; Owls Application Notes No. 004; 2006; one page; located at www.owls-sensors.com/; Microvacuum.

Rossato et al.; "Sperm treatment with extracellular ATP increases fertilization rates in in-vitro fertilization for male factor infertility"; Human Reproduction; 1999; pp. 694-697; vol. 14, No. 3; European Society of Human Reproduction and Embryology.

(56) References Cited

OTHER PUBLICATIONS

Savran et al.; "Micromechanical Detection of Proteins Using Aptamer-Based Receptor Molecules"; Anal. Chem.; Jun. 1, 2004; pp. 3194-3198; vol. 76, No. 11; American Chemical Society.
Small et al ; "Immunotherapy of Hormone-Refractory Prostate Cancer With Antigen-Loaded Dendritic Cells"; Journal of Clinical Oncology; Dec. 1, 2000; pp. 3894-3903; vol. 18, No. 23; American Society of Clinical Oncology.
Stelzle et al.; "Sensitive detection of protein adsorption to supported lipid bilayers by frequency-dependent capacitance measurements and microelectrophoresis"; Biochimica et Biophysica Acta.; 1989; pp. 135-142; vol. 981; Elsevier Science Publishers B.V.
Vodyanik et al.; "Human embryonic stem cell-derived CD34+ cells: efficient production in the coculture with OP9 stromal cells and analysis of lymphohematopoietic potential"; Blood; Jan. 15, 2005; pp. 617-626; vol. 105, No. 2; The American Society of Hematology.
Yan et al.; "Directed Differentiation of Dopaminergic Neuronal Subtypes from Human Embryonic Stem Cells"; Stem Cells; 2005; pp. 781-790; vol. 23, No. 6; AlphaMed Press.
Yu et al.; "Specific T Regulatory Cells Display Broad Suppressive Functions against Experimental Allergic Encephalomyelitis upon Activation with Cognate Antigen"; The Journal of Immunology; 2005; pp. 6772-6780; vol. 174; The American Association of Immunologists, Inc.
Zeng et al.; "Synergy of IL-21 and IL-15 in regulating CD8+ T cell expansion and function"; JEM; Jan. 3, 2005; pp. 139-148; vol. 201, No. 1.

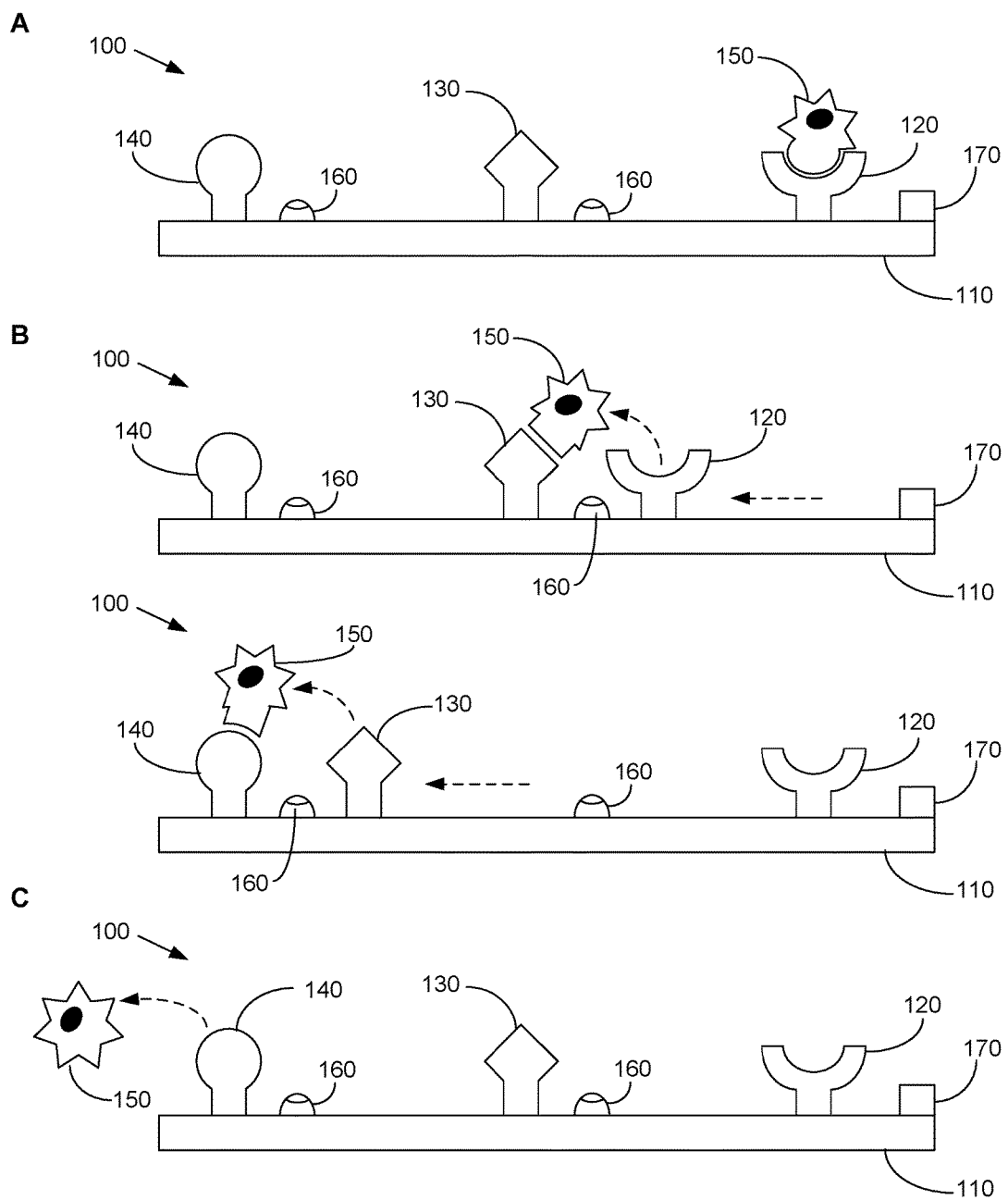

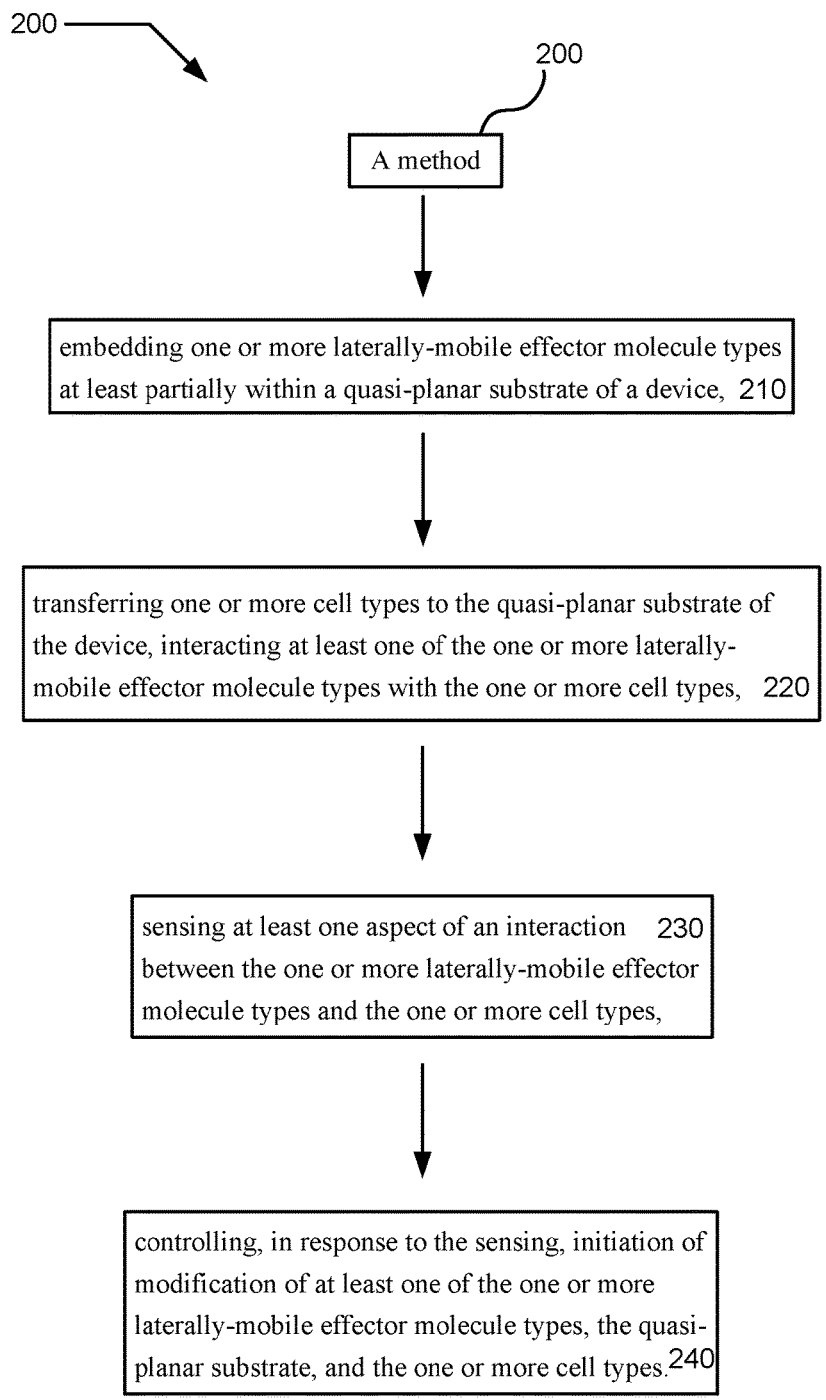

DEVICE, SYSTEM, AND METHOD INCLUDING MICRO-PATTERNED CELL TREATMENT ARRAY

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)).

PRIORITY APPLICATIONS

The present application constitutes a divisional of U.S. patent application Ser. No. 13/200,496, entitled DEVICE, SYSTEM, AND METHOD INCLUDING MICRO-PATTERNED CELL TREATMENT ARRAY, naming Roderick A. Hyde and Lowell L. Wood, Jr. as inventors, filed 23 Sep. 2011, which is currently co-pending or is an application of which a currently co-pending application is entitled to the benefit of the filing date, and which is a continuation of U.S. patent application Ser. No. 13/135,130, entitled DEVICE, SYSTEM, AND METHOD INCLUDING MICRO-PATTERNED CELL TREATMENT ARRAY, naming Roderick A. Hyde and Lowell L. Wood, Jr. as inventors, filed 24 Jun. 2011.

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

Devices, systems, and methods are disclosed herein for treatment of disease involving one or more cell types in a vertebrate subject. The device can responsively interact with the one or more cell types to modify or differentiate the one or more cell types in the vertebrate subject, or to induce apoptosis or necrosis in the one or more cell types in the vertebrate subject. The cell types can include one or more of immune cells, pathogens, pathologic cells, tumor cells, neoplastic cells, or defective cells. A device is disclosed that includes a quasi-planar substrate; and one or more laterally-mobile effector molecule types at least partially embedded within the quasi-planar substrate, wherein at least one of the one or more laterally-mobile effector molecule types is configured to interact with one or more cell types. The device can further include one or more sensors configured to detect at least one aspect of an interaction between the at least one of the one or more laterally-mobile effector molecule types and the one or more cell types; and a controller in communication with the one or more sensors, wherein the controller is configured to responsively initiate modification of at least one of the one or more laterally-mobile effector molecule types, the quasi-planar substrate, and the one or more cell types. The device can responsively interact with eukaryotic cells or prokaryotic cells to modify, differentiate, or kill the cells.

At least one of the one or more effector molecule type can include, but is not limited to, a ligand molecule, a receptor molecule, or a cytokine. The one or more laterally-mobile effector molecule types modified in response to the controller can be configured to be different from the one or more laterally-mobile effector molecule types sensed interacting with the one or more cell types by the one or more sensors. The at least two of the one or more laterally-mobile effector molecule types can be configured such that the one or more cell types interact sequentially with the at least two of the one or more laterally-mobile effector molecule types. The at least two of the one or more laterally-mobile effector molecule types can be configured such that the one or more cell types interact simultaneously with the at least two of the one or more laterally-mobile effector molecule types. The controller can be configured to responsively add at least one of the one or more laterally-mobile effector molecule types to the quasi-planar substrate. The controller can be configured to responsively remove at least one of the one or more laterally-mobile effector molecule types from the quasi-planar substrate. The quasi-planar substrate can include one or more discreet regions configured to include at least one of the one or more laterally-mobile effector molecule types. The controller can be configured to responsively move at least one of the one or more laterally-mobile effector molecule types and the one or more cell types relative to the quasi-planar substrate. The controller can be configured to responsively remove at least one of the one or more laterally-mobile effector molecule types and the one or more cell types from the quasi-planar substrate.

The quasi-planar substrate can include a liquid configured as an interface with a cell type-carrying fluid. The liquid can be configured to at least partially embed the one or more laterally-mobile effector molecule types on the quasi-planar substrate. The quasi-planar substrate can include a membrane. The membrane can be bordered by a solid substrate. The membrane can include a lipid bilayer. The membrane can include a lipid monolayer. The membrane can be configured to contact a liquid or solid surface within the quasi-planar substrate. The cell type-carrying fluid can include, but is not limited to, a gas or a liquid. The quasi-planar substrate can include a solid surface configured to at least partially embed at least one of the one or more laterally-mobile effector molecule types. The quasi-planar substrate can include a liquid at least partially surrounding the solid surface, wherein the liquid is configured to at least partially embed at least one of the one or more laterally-mobile effector molecule types within the liquid. The quasi-planar substrate can be configured to mobilize at least one of the one or more laterally-mobile effector molecule types in essentially two dimensions on the quasi-planar substrate. The quasi-planar substrate can be configured to bi-directionally mobilize at least one of the one or more laterally-mobile effector molecule types in essentially one dimension on the quasi-planar substrate. The quasi-planar substrate can be configured to include one or more spatially-discrete portions. At least one of the one or more spatially-discrete portions can include two or more identical of the one or more laterally-mobile effector molecule type. At least one of the one or more spatially-discrete portions can include two or more different of the one or more laterally-mobile effector molecule type. The one or more spatially-discrete portions can include one or more of array sites or channels. The one or more spatially-discrete portions can be connected with a fluidic interface. The controller can include one or more of static connections or dynamic connections, wherein the one or more of the static connections or the dynamic connections are configured to control communication between the one or more spatially discrete portions. The one or more of the static connections or the dynamic connections can be fluid connections.

The one or more laterally-mobile effector molecule can include, but is not limited to, one or more of protein, oligonucleotide, or aptamer. The one or more laterally-mobile effector molecule can include, but is not limited to, one or more of antibody, B cell receptor, T cell receptor, major histocompatibility complex (MHC) protein, antigen-loaded MHC protein, co-stimulatory molecule, or cytokine. The interaction between the one or more laterally-mobile effector molecule types and the one or more cell types can include interaction with a receptor on the one or more cell types. At least one of the one or more laterally-mobile effector molecule types can be configured to undergo a conformational change in response to interaction with the one or more cell types. At least one of the one or more laterally-mobile effector molecule types can be configured to react with one or more binding components in response to interaction with the one or more cell types. The one or more binding components can include, but is not limited to, protein, antibody, receptor, ligand, major histocompatibility complex (MHC), antigen-loaded MHC, co-stimulatory molecule, oligonucleotide, aptamer, or cytokine. The one or more binding components can be laterally mobile in the substrate. The one or more binding components can be mobile in a liquid of the substrate. The one or more binding components can be a component of intracellular signaling. The one or more binding components can be on the one or more cell types. At least one of the one or more laterally-mobile effector molecule types can be configured to bind and interact with a single cell type of the one or more cell types. The controller can be configured to responsively interact with the single cell type. The single cell type can include, but is not limited to, one or more of T cells, B cells, dendritic cells, NK cells, macrophages, phagocytes, monocytes, lymphocytes, macrophages, neutrophils, granulocytes, eosinophils, basophils, mast cells, stem cells, or germ-line cells. The controller can be configured to responsively modify the single cell type. The controller can be configured to responsively modify the single cell type by one or more of activating B cells, activating T cells, changing cell status to memory cell or from memory cell, altering cytokine expression profiles, inducing affinity maturation, inducing hyper-affinity maturation, or inducing or changing stem cell differentiation. The controller can be configured to responsively modify the single cell type by inducing anergy, removing anergy, inducing apoptosis, or inducing necrosis. The sensor can be configured to identify the single cell type, and the controller can be configured to modify the single cell type. The one or more laterally-mobile effector molecules can include a fluorescent component.

The one or more sensors can include, but is not limited to, a mass sensor, force sensor, weight sensor, or surface vibration sensor. The one or more sensors can include, but is not limited to, optical sensor, plasmonic sensor, electrical sensor, capacitive sensor, or chemical sensor. The one or more sensors can be configured to spatially detect at least one of the one or more laterally-mobile effector molecule types and at least one of the one or more cell types in one or more spatially-discrete portions of the quasi-planar substrate. The one or more sensors can be configured to detect one or more interactions of at least one of the one or more laterally-mobile effector molecule types with at least one of the one or more cell types, wherein the one or more interactions occur at the one or more spatially-discrete portions of the quasi-planar substrate. The one or more sensors can be configured to detect a position of at least one of the one or more cell types bound to the quasi-planar substrate. The one or more sensors can be configured to detect a position of the one or more laterally-mobile effector molecule types on the quasi-planar substrate. The controller can be configured to respond in one or more of a real-time response, in a delayed response, in a sequenced response, or in a response dependent upon a combination of previously-sensed interactions. At least one of the one or more laterally-mobile effector molecule types can be configured to increase binding of at least one of the one or more cell types to the quasi-planar substrate. At least one of the one or more laterally-mobile effector molecule types can be configured to decrease binding of at least one of the one or more cell types to the quasi-planar substrate.

The controller can be configured to direct motion of at least one of the one or more laterally-mobile effector molecule types toward or away from at least one of the one or more cell types. The controller can be configured to interact with at least one of a magnetic component, an electrical component, or an optical component of the one or more laterally-mobile. The controller can be configured to respond by introducing one or more components into or onto at least one of the one or more cell types. The controller can be configured to respond by introducing one or more components into or onto at least one of the one or more cell type by endocytosis, transfection, transformation, electroporation, diffusion, pore transport, active membrane transport, passive membrane transport, or membrane-to-membrane transfer. The one or more components can be configured to allow at least one of the one or more cell type to be subsequently acted upon, tracked, identified, or killed. The one or more components can include one or more of genetic material, chemical entity, nucleic acid, protein, lipid, virus, vesicle, detectable tag, QDOT, or magnetic nanoparticle. The controller can be configured to respond by applying energy in the form of one or more of light, heat, magnetism, pressure, electricity, or vibration. The controller can be configured to respond by applying fluidic force or motional force to the one or more laterally-mobile effector molecule types or the quasi-planar substrate. The force can be transferred to the cell by one or more bound laterally-mobile effector molecule types. The controller can be configured to respond by applying the fluidic force or the motional force utilizing one or more of outflow pump, intake pump, surface tension, electrical force, laser light-induced force, or magnetic force. The controller can be configured to respond by applying motional force to the one or more cell types. The controller can be configured to respond by altering connectivity of the quasi-planar substrate. The controller can be configured to respond by altering MEMS barriers on the quasi-planar substrate. The controller can be configured to move at least one of the one or more cell types between one or more spatially discrete portions of the quasi-planar substrate. The one or more spatially discrete portions of the quasi-planar substrate can be configured to perform one or more actions on at least one of the one or more cell types, expose the one or more cell types to different environments, or collect the one or more cell types into a common site. The controller can be configured to rotate at least one of the one or more cell types to a new orientation. The controller can be configured to rotate at least one of the one or more cell types by differential binding or release at one or more different sites on the at least one of the one or more cell types. The controller can be configured to expose different cell regions or cell receptors to the quasi-planar substrate. The controller can be configured to respond to binding of at least one of the one or more cell types at one region of the quasi-planar substrate by altering a configuration of the one or more laterally-mobile effector molecule types at a second region on the quasi-planar substrate. The device can further include one or more fluid bypasses configured to receive and process at least one of the one or more cell types in one or more fluids from a vertebrate subject through the device and configured to return processed fluids through the one or more fluid bypasses into the vertebrate subject.

A method is disclosed that includes embedding one or more laterally-mobile effector molecule types at least partially within a quasi-planar substrate of a device, transferring one or more cell types to the quasi-planar substrate of the device, interacting at least one of the one or more laterally-mobile effector molecule types with the one or more cell types, sensing at least one aspect of an interaction between the one or more laterally-mobile effector molecule types and the one or more cell types, and controlling, in response to the sensing, initiation of modification of at least one of the one or more laterally-mobile effector molecule types, the quasi-planar substrate, and the one or more cell types. At least one of the one or more effector molecule type can include, but is not limited to, a ligand molecule, a receptor molecule, or a cytokine. The one or more laterally-mobile effector molecule types modified in response to the controller can be configured to be different from the one or more laterally-mobile effector molecule types sensed interacting with the one or more cell types by the one or more sensors.

The method can include interacting the one or more cell types with at least two of the one or more laterally-mobile effector molecule types such that the one or more cell types interact sequentially with the at least two of the one or more laterally-mobile effector molecule types. The method can include interacting the one or more cell types with at least two of the one or more laterally-mobile effector molecule types such that the one or more cell types interact simultaneously with the at least two of the one or more laterally-mobile effector molecule types. In the method, controlling movement can include adding at least one of the one or more laterally-mobile effector molecule types to the quasi-planar substrate. The quasi-planar substrate can include one or more discreet regions configured to include at least one of the one or more laterally-mobile effector molecule types. In the method, controlling movement can include removing at least one of the one or more laterally-mobile effector molecule types from the quasi-planar substrate. In the method, controlling movement can include moving at least one of the one or more laterally-mobile effector molecule types and the one or more cell types on the quasi-planar substrate. In the method, controlling movement can include removing at least one of the one or more laterally-mobile effector molecule types and the one or more cell types from the quasi-planar substrate.

In the method, the quasi-planar substrate can include a liquid configured as an interface with a cell type-carrying fluid. The method can include embedding at least one of the one or more laterally-mobile effector molecule types in the liquid of the quasi-planar substrate. The quasi-planar substrate can include a membrane. The membrane can be bordered by a solid substrate. The method can include contacting a liquid surface or a solid surface of the quasi-planar substrate with the membrane. The method can include mobilizing at least one of the one or more laterally-mobile effector molecule types in essentially two dimensions on the quasi-planar substrate. The method can include bi-directionally mobilizing at least one of the one or more laterally-mobile effector molecule types in essentially one dimension on the quasi-planar substrate. The quasi-planar substrate can be configured to include one or more spatially-discrete portions. In the method, each of the one or more spatially-discrete portions can include two or more identical of the one or more laterally-mobile effector molecule type. In the method, each of the one or more spatially-discrete portions can include two or more different of the one or more laterally-mobile effector molecule type. The one or more spatially-discrete portions can include one or more of array sites or channels. The method can include fluidically connecting the one or more spatially-discrete portions. The method can include controlling communication between the one or more spatially discrete portions with one or more of static connections or dynamic connections. The one or more of static connections or the dynamic connections can be fluid connections.

The method can include inducing a conformational change in at least one of the one or more laterally-mobile effector molecule types in response to interaction with the one or more cell types. In the method, at least one of the one or more laterally-mobile effector molecule types can be configured to bind and interact with a single cell type of the one or more cell types. The method can include identifying the single cell type by one or more sensors, and modifying the single cell type in response to action of the controller. The method can include spatially detecting at least one of the one or more laterally-mobile effector molecule types and the one or more cell types in one or more spatially-discrete portions of the quasi-planar substrate with one or more sensors. The method can include detecting one or more responsive interactions of at least one of the one or more laterally-mobile effector molecule types with the one or more cell types by the one or more sensors, wherein the one or more responsive interactions occur at the one or more spatially-discrete portions of the quasi-planar substrate. The method can include detecting a position of the one or more cell types bound to the quasi-planar substrate by the one or more sensors. The method can include introducing at least one of the one or more laterally-mobile effector molecule types to the quasi-planar substrate by response of the controller. The method can include removing at least one of the one or more laterally-mobile effector molecule types from the quasi-planar substrate by response of the controller. In the method, at least one of the one or more laterally-mobile effector molecule types can be configured to increase binding of the one or more cell types to the quasi-planar substrate. In the method, at least one of the one or more laterally-mobile effector molecule types can be configured to decrease binding of the one or more cell types to the quasi-planar substrate. In the method, the controlling can be configured to direct motion of at least one of the one or more laterally-mobile effector molecule types toward or away from the one or more cell types. In the method, the controlling can be configured to direct application of fluidic force or motional force to at least one of the one or more laterally-mobile effector molecule types or the quasi-planar substrate.

In the method, the controlling can be configured to direct alteration of connectivity of the quasi-planar substrate. In the method, the controlling can be configured to direct alteration of MEMS barriers on the quasi-planar substrate. In the method, the controlling can be configured to direct alteration of movement the one or more cell types between one or more spatially discrete portions of the quasi-planar substrate. In the method, the controlling can be configured to direct alteration of rotation of the one or more cell types to a new orientation. In the method, the controlling can be configured to respond to binding of the one or more cell types at one region of the quasi-planar substrate by directing alteration of a configuration of at least one of the one or more laterally-mobile effector molecule types at a second region on the quasi-planar substrate. The method can include receiving and processing one or more cell types in one or more fluids from a vertebrate subject through one or more fluid bypasses of the device and returning processed fluids through the one or more fluid bypasses into the vertebrate subject through the one or more fluid bypasses.

A system is disclosed that includes a fluid bypass configured to passage fluids including one or more cell types from a vertebrate subject into a device and configured to return the passaged fluids to the vertebrate subject, wherein the device includes a quasi-planar substrate; and one or more laterally-mobile effector molecule types at least partially embedded within the quasi-planar substrate, wherein the one or more laterally-mobile effector molecule types is configured to interact with one or more cell types; one or more sensors configured to detect the at least one aspect of the interaction between the one or more laterally-mobile effector molecule types and the one or more cell types; and a controller in communication with the one or more sensors, wherein the controller is configured to responsively initiate modification of at least one of the one or more laterally-mobile effector molecule types, the quasi-planar substrate, and the one or more cell types. At least one of the one or more effector molecule type can include, but is not limited to, a ligand molecule, a receptor molecule, or a cytokine. The one or more laterally-mobile effector molecule types modified in response to the controller can be configured to be different from the one or more laterally-mobile effector molecule types sensed interacting with the one or more cell types by the one or more sensors.

The at least two of the one or more laterally-mobile effector molecule types can be configured such that the one or more cell types interact sequentially with the at least two of the one or more laterally-mobile effector molecule types. The at least two of the one or more laterally-mobile effector molecule types can be configured such that the one or more cell types interact simultaneously with the at least two of the one or more laterally-mobile effector molecule types. The controller can be configured to responsively add at least one of the one or more laterally-mobile effector molecule types to the quasi-planar substrate. The controller can be configured to responsively remove at least one of the one or more laterally-mobile effector molecule types from the quasi-planar substrate. The quasi-planar substrate can include one or more discreet regions configured to include at least one of the one or more laterally-mobile effector molecule types.

The controller can be configured to responsively move at least one of the one or more laterally-mobile effector molecule types and the one or more cell types relative to the quasi-planar substrate. The controller can be configured to responsively remove at least one of the one or more laterally-mobile effector molecule types and the one or more cell types from the quasi-planar substrate.

The quasi-planar substrate can include a liquid configured as an interface with a cell type-carrying fluid. The liquid can be configured to at least partially embed the one or more laterally-mobile effector molecule types on the quasi-planar substrate. The quasi-planar substrate can include a membrane. The membrane can be bordered by a solid substrate. The membrane can include a lipid bilayer. The membrane can include a lipid monolayer. The membrane can be configured to contact a liquid or solid surface within the quasi-planar substrate.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 1A, 1B, and 1C depict a diagrammatic view of an aspect of an embodiment of a device.

FIG. 2 depicts a logic flowchart of a method for treating a disease or condition in a vertebrate subject.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Devices, systems, and methods are disclosed herein for treatment of disease involving one or more cell types in a vertebrate subject. The device can responsively interact with the one or more cell types to modify or differentiate the one or more cell types in the vertebrate subject, or to induce apoptosis or necrosis in the one or more cell types in the vertebrate subject. The cell types can include one or more of immune cells, pathogens, pathologic cells, tumor cells, neoplastic cells, or defective cells. A device is disclosed that includes a quasi-planar substrate; and one or more laterally-mobile effector molecule types at least partially embedded within the quasi-planar substrate, wherein at least one of the one or more laterally-mobile effector molecule types is configured to interact with one or more cell types. The device can further include one or more sensors configured to detect at least one aspect of an interaction between the at least one of the one or more laterally-mobile effector molecule types and the one or more cell types; and a controller in communication with the one or more sensors, wherein the controller is configured to responsively initiate modification of at least one of the one or more laterally-mobile effector molecule types, the quasi-planar substrate, and the one or more cell types. The device can responsively interact with eukaryotic cells or prokaryotic cells to modify, differentiate, or kill the cells.

The device includes a quasi-planar substrate that can incorporate one or more fixed or laterally-mobile effector molecules that bind to cell surface components on the one or more cell types. The quasi-planar substrate can include a liquid configured as an interface with a cell type-carrying fluid. The liquid can be configured to at least partially embed the one or more laterally-mobile ligand types. The liquid can include a membrane, e.g., a lipid bilayer or a lipid monolayer. The membrane can be configured to contact a liquid or solid surface of the quasi-planar substrate. The laterally-mobile effector molecule types can include one or more of ligand molecules, receptor molecules, or cytokines. The device includes one or more sensors configured to detect the one or more laterally-mobile effector molecule types and the one or more cell types and can detect cell binding to at least one of the one or more laterally-mobile effector molecule types on the substrate. The one or more sensors can signal to a controller configured to responsively initiate movement of the one or more laterally-mobile effector molecule types and the one or more cell types in the quasi-planar substrate. The controller can responsively interact with the sensor to modify the one or more cell types by sequentially exposing at least one of the laterally-mobile effector molecules to the one or more cell types. The device includes a quasi-planar solid support and multiple discreet regions or multiple reaction compartments on the quasi-planar solid support. The device includes a fluid media with at least partially embedded laterally-mobile effector molecules, e.g., one or more of ligand molecules, receptor molecules, or cytokines, and sensors to detect interaction of the at least partially embedded laterally-mobile effector molecules with the one or more cell types. An external media in contact with the laterally-mobile effector molecules and the sensors on the quasi-planar solid support is configured to transport the one or more cell types between reaction compartments. The interface between the quasi-planar solid support and the fluid media can be maintained, e.g., by gravity, by surface tension, or by liquid-liquid immiscibility.

The device disclosed herein can be used to modify functional cells, e.g., immune cells, effector cells, or receptor cells, in a vertebrate subject or to inactivate or kill pathogens, pathologic cells, tumor cells, neoplastic cells, or defective cells in a vertebrate subject. Cell refers to any cell or cells, as well as viruses, virus-infected cells, or other particles having a size that is similar to that of a biological cell, including any prokaryotic cell, e.g., bacteria, or eukaryotic cell, e.g., fungi, plant cells or animal cells. Cells can typically be spherical, or can be elongated, flattened, deformable or asymmetrical, i.e., not spherical. The size or diameter of a cell typically ranges from about 0.1 µm to 120 µm, or is from about 1 µm to 50 µm. Cells modified by the device as described herein can be useful for immunotherapy, cancer therapy, anti-infective agents, regenerative medicine, transplantation, reproductive biology, drug discovery, gene discovery, and other clinical, biotechnology, or research uses. For immunotherapy, the device as described herein can be used to differentiate, mature, activate, induce anergy, load antigen, electroporate or transduce cells. Immune cells can be T lymphocytes, B lymphocytes, natural killer (NK) cells, lymphokine-activated killer (LAK) cells, dendritic cells, macrophages, monocytes, granulocytes, Kupffer cells, Langerhans cells, and other immune cell types. T lymphocytes activated by the device can be helper T cells ($T_H$, $T_H1$, $T_H2$, $T_H17$), cytolytic T cells, or regulatory T cells. For example, $T_H$ cells can be activated by laterally mobile membrane proteins protruding from a lipid bilayer of the device. A method is disclosed that includes embedding one or more laterally-mobile effector molecule types at least partially within a quasi-planar substrate of a device, transferring one or more cell types to the quasi-planar substrate of the device responsively interacting at least one of the one or more laterally-mobile effector molecule types sequentially with the one or more cell types, wherein at least one of the one or more laterally-mobile effector molecule types is configured to interact sequentially with the one or more cell types sensing at least one of the one or more laterally-mobile effector molecule types interacting with the one or more cell types, and responsively controlling movement of at least one of the one or more laterally-mobile effector molecule types and the one or more cell types in the quasi-planar substrate.

A system is disclosed that includes a fluid bypass configured to passage fluids including one or more cell types from a vertebrate subject into a device and configured to return the passaged fluids to the vertebrate subject, wherein the device includes a quasi-planar substrate; and one or more laterally-mobile effector molecule types at least partially embedded within the quasi-planar substrate, wherein at least one of the one or more laterally-mobile effector molecule types is configured to interact with one or more cell types; one or more sensors configured to detect at least one aspect of an interaction between the at least one of the one or more laterally-mobile effector molecule types and the one or more cell types; and a controller in communication with the one or more sensors, wherein the controller is configured to responsively initiate modification of at least one of the one or more laterally-mobile effector molecule types, the quasi-planar substrate, and the one or more cell types.

With reference to the figures, and with reference now to FIGS. 1 and 2 depicted is one aspect of a device, a method, or a system that may serve as an illustrative environment of and/or for subject matter technologies, for example, a device including a quasi-planar substrate; and one or more laterally-mobile effector molecule types embedded within the quasi-planar substrate, wherein the one or more laterally-mobile effector molecule types is configured to responsively interact with one or more cell types, and the one or more cell types interacts sequentially with one or more of the one or more laterally-mobile effector molecule types. Accordingly, the present disclosure describes certain specific devices or systems of FIGS. 1 and 2; and describes embodiments including certain specific devices, methods, and systems. Those having skill in the art will appreciate that the specific devices or systems described herein are intended as merely illustrative of their more general counterparts.

Referring to FIGS. 1A, 1B, and 1C, depicted is a partial diagrammatic view of one aspect of an embodiment of a device 100 including a quasi-planar substrate 110; and one or more laterally-mobile effector molecule types 120, 130, 140 embedded within the quasi-planar substrate 110, wherein the one or more laterally-mobile effector molecule types 120, 130, 140 is configured to responsively interact with one or more cell types 150, and at least one of the one or more laterally-mobile effector molecule types 120, 130, 140 is configured to interact sequentially with the one or more cell types 150. The effector molecule type can be a ligand molecule 120. The effector molecule type can be a receptor molecule 130. The effector molecule type can be a cytokine 140. The device can further include one or more sensors 160 configured to detect the at least one of the one or more laterally-mobile effector molecule types 120, 130, 140 interacting with the one or more cell types 150; and a controller 170 in communication with the one or more sensors 160, wherein the controller 170 is configured to responsively initiate modification or movement of the one or more laterally-mobile effector molecule types 120, 130, 140 and the one or more cell types 150 in the quasi-planar substrate 110.

Referring to FIG. 1A, depicted is a partial diagrammatic view of an aspect of an embodiment of a device 100 including a quasi-planar substrate 110; and one or more laterally-mobile effector molecule types 120, 130, 140 embedded within the quasi-planar substrate 110, wherein the one or more laterally-mobile effector molecule types, e.g., a ligand molecule 120, is configured to responsively interact with one or more cell types 150.

Referring to FIG. 1B, depicted is a partial diagrammatic view of an aspect of an embodiment of a device 100 including a quasi-planar substrate 110; and one or more laterally-mobile effector molecule types 120, 130, 140 embedded within the quasi-planar substrate 110, wherein the one or more laterally-mobile effector molecule types, e.g., a receptor molecule 130, is configured to responsively interact with the one or more cell types 150. The one or more sensors can sense an interaction between the ligand molecule 120 and the one or more cell types 150. The controller 170 in communication with the one or more sensors 160 is configured to responsively initiate modification or movement of the ligand molecule 120 and the one or more cell types 150 in the quasi-planar substrate 110 such that the one or more cell types 150 can interact with a second laterally-mobile effector molecule types, e.g., a receptor molecule 130.

Referring to FIG. 1C, depicted is a partial diagrammatic view of an aspect of an embodiment of a device 100 including a quasi-planar substrate 110; and one or more laterally-mobile effector molecule types 120, 130, 140 embedded within the quasi-planar substrate 110, wherein the one or more laterally-mobile effector molecule types, e.g., a cytokine 140, is configured to responsively interact with the one or more cell types 150. The one or more sensors can sense an interaction between the receptor molecule 130 and the one or more cell types 150. The controller 170 in communication with the one or more sensors 160 is configured to responsively initiate modification or movement of the receptor molecule 130 and the one or more cell types 150 in the quasi-planar substrate 110 such that the one or more cell types 150 can interact with a third laterally-mobile effector molecule types, e.g., a cytokine molecule 140. The one or more cell types 150 interact with the cytokine molecule 140 and are subsequently released from the interaction with the cytokine molecule 140.

Referring to FIG. 2, depicted is a partial diagrammatic view of one aspect of an embodiment of a method 200 including embedding 210 one or more laterally-mobile effector molecule types at least partially within a quasi-planar substrate of a device, transferring 220 one or more cell types to the quasi-planar substrate of the device, interacting at least one of the one or more laterally-mobile effector molecule types with the one or more cell types, sensing 230 at least one aspect of an interaction between the one or more laterally-mobile effector molecule types and the one or more cell types, and controlling 240, in response to the sensing, initiation of modification of at least one of the one or more laterally-mobile effector molecule types, the quasi-planar substrate, and the one or more cell types.

The device can include one or more laterally-mobile effector molecule types at least partially embedded within the quasi-planar substrate that are activating receptors for $T_H$ cells that comprise an immune synapse, including for example, a viral peptide antigen complexed with MHC class II; costimulatory molecules, e.g., CD4, CD80 or CD86; and integrins, e.g., ICAM-1. The device can act as an immune synapse to stimulate T cells. See e.g., Doh and Irvine, *Proc. Natl. Acad. Sci. USA* 103: 5700-5705, 2006, which is incorporated herein by reference. The device can further deliver one or more laterally-mobile effector molecule types at least partially embedded within the quasi-planar substrate that include cytokines, e.g., IL-2, IL-12, or IFN-γ, to the $T_H$ cell in response to signals from sensors in the device indicating that a $T_H1$ cell has bound to activating receptors such as those described above which comprise an immune synapse. Alternatively, autoreactive T cells or pathogenic T cells can be selectively inactivated or killed by processing in the device. For example, autoreactive $CD8^+$ T cells can be selectively engaged by MHC class I plus an autoantigen peptide, e.g., a peptide from myelin basic protein (MBP). MHC I plus MBP-peptide complex can be presented on the surface of the phospholipid bilayer of the device and bind autoreactive T cells. T cell binding to the MHC plus MBP-peptide complex can activate a sensor (e.g., a surface plasmon resonance sensor that initiates an electrical signal to a controller. The controller can respond by inducing apoptosis in the $CD8^+$ T cell. The controller can actuate valves and pumps to deliver anti-Fas receptor (FasR, CD95) antibody to induce apoptosis in the engaged T cell. Alternatively, the controller can respond by presenting the membrane protein, Fas ligand (FasL, CD178) on the surface of the bilayer to engage FasR and induce apoptosis in the $CD8^+$ T cell. See, e.g., Holler et al., *Mol. Cell. Biol.* 23: 1428-1440, 2003 which is incorporated herein by reference.

The device as described herein can be used to transfect, grow, induce, activate, de-differentiate or differentiate stem cells for applications in regenerative medicine. Stem cells including, but not limited to, hematopoietic stem cells, myeloid stem cells, mesenchymal stem cells, embryonic stem cells (ESC) and induced pluripotent stem cells (iPSCs) can be used for transplantation to treat autoimmune diseases, cancer, and many other diseases. For example the device can be used to reprogram (i.e. de-differentiate) adult human fibroblasts to become iPSCs by microinjecting the transcription factors: Oct 4, Sox 2, Klf 4 and Myc. See e.g., Graf and Enver, "Forcing cells to change lineages." *Nature* 462: 587-594, 2009 which is incorporated herein by reference. Alternatively, stem cells can be differentiated and/or cultivated in the device to generate specific cell lineages. The specific cell lineages, neuronal cells, or hematopoietic cells can be used to treat patients with neurodegenerative diseases or hematological cancers, respectively. The device can be used to differentiate ESC to become neuroepithelial cells and then dopamine (DA) neurons. See e.g., Yan et al., "Directed differentiation of dopaminergic neuronal subtypes from human embryonic stem cells." *Stem Cells* 23: 781-790, 2005 which is incorporated herein by reference. ESCs can be grown in the device in a neural growth media containing fibroblast growth factor-2 to generate neural epithelial cells. The neural epithelial cells can then be moved to a cell bay containing a laminin substrate and treated with sonic hedgehog and fibroblast growth factor-8 to generate DA neurons. The device can detect DA released into the media by DA neurons and also sense the expression of neuron-specific marker proteins such as synaptophysin and c-Ret indicating functional DA neurons have differentiated. A controller can respond to signals from the neuronal cell sensors by transporting the differentiated DA neurons to a collection compartment where they can be harvested for transplantation to Parkinson's disease patients whose DA neurons have degenerated.

The device can also be used to obtain hematopoietic progenitor cells that can be used for transplantation into leukemia and lymphoma patients to regenerate the hematopoietic systems of the patients. To obtain autologous, i.e., "matched" stem cells the device can be used to produce iPSCs by reprogramming a patient's fibroblasts as described above. See e.g., Graf and Enver, Ibid. and Choi et al., "Hematopoietic and endothelial differentiation of human induced pluripotent stem cells." *Stem Cells* 27: 559-567, 2009, which are incorporated herein by reference. The iPSCs are differentiated to hematopoietic progenitor cells by growth in the device over a feeder layer of bone marrow stromal cells, e.g., OP9 cells. See Vodyanik et al., *Blood* 105: 617-626, 2005 which is incorporated herein by reference. After culture for approximately 8 days the device can detect and collect hematopoietic progenitors (CD34$^+$CD43$^+$ cells; see e.g., Choi et al., Ibid.) which can be used to repopulate multiple hematopoietic lineages in leukemia and lymphoma patients undergoing bone marrow transplantation.

The device as described herein can be used to cultivate and fertilize mammalian oocytes prior to implantation. Oocytes can be retrieved by transvaginal aspiration and cultured in the device with human tubal fluid medium at 37° C. For fertilization, approximately $10^5$ motile sperm can be injected into a cell bay containing an oocyte, and fertilization is allowed to proceed for approximately 16-20 hours. See e.g., Rossato et al., *Hum. Reprod.* 14: 694-697, 1999 which is incorporated herein by reference. The device can detect pronuclei in fertilized oocytes microscopically and with optical sensors. After 46-48 hours the device can also detect cell cleavage and evaluate embryo quality. Optical sensors in the device signal a controller when high quality embryos are detected. The controller can actuate microfluidics including micropumps and valves in the device to transport and collect embryos for implantation.

The device as described herein can be constructed with a quasiplanar substrate including a solid substrate supporting a fluid substrate that includes laterally-mobile ligand molecules and sensors. The ligands and sensors can detect and engage cells in the device and signal to a controller. The solid substrate can be comprised of silica, glass, polydimethylsiloxane, plastic, metal, fiber, or membrane. A micropattern array on the solid substrate can be formed using microfabrication techniques such as photolithography, acid etching, soft lithography, or drilling. For instance, micromachining techniques include film deposition processes, such as sputtering, spin coating in combination with chemical vapor deposition, laser fabrication, photolithographic techniques, or etching methods. Etching can be performed by wet chemical, plasma, reactive ion or sputtering processes. Micromachining methods are described, for example, in Petersen, *Proceedings of the IEEE* 70: 420-457, 1982, which is incorporated herein by reference. Methods can be used to construct microfluidic channels, cell bays, on-chip pumps, piezoelectric actuators, optical tweezers, valves and reservoirs in microchips. See, e.g., U.S. Pat. No. 7,435,578 issued to Wikswo et al. on Oct. 14, 2008 and Enger et al., *Lab Chip* 4: 196-200, 2004, which are incorporated herein by reference. For example, the microfluidics layer can be fusion bonded to a silicon layer containing sensing and control elements. The microfluidics layer can include channels, cell chambers and silicon containers with submicron holes. The channels and containers are etched into the substrate by reactive ion etching of a silicon nitride mask and a non-isotropic potassium hydroxide (KOH) etch. Alternatively, the micropattern array device can be constructed using a soft lithography process. See e.g., Liu et al., *Lab Chip* 9: 1200-1205, 2009 which is incorporated herein by reference. A microfluidic device can be constructed from polydimethylsiloxane (PDMS) using a liquid-molding procedure to create interconnected channels, single cell bays, reservoirs, valves, gates and cell collection traps. Photolithography can be used to fabricate glycerol molds that can be used to cast PDMS microchips. The microchips can be drilled to create access holes, or to install pumps, valves or gates. The device can include phospholipid bilayers, ligands, sensors and electrodes added to the cell bays. The microfluidics can be enclosed by bonding the PDMS microchip to a glass slide. Channels with a width ranging from approximately 50 µm to 500 µm and an apical height ranging from approximately 10 µm to 50 µm can be created to connect cell chambers, reservoirs, cell collection traps and external ports. Multiple parallel microfluidic circuits can be created in a 25 mm×75 mm microchip. See e.g., Liu et al., Ibid. The device can include on-chip pumps constructed from a reservoir covered with a flexible membrane. The flexible membrane can be moved in or out by changing the length of a piezoelectric element to pump fluid through the reservoir. An array of individually addressable piezoelectric filaments can be utilized to provide separate actuation of multiple pumps. The piezoelectric filaments can also provide valving by pinching closed sections of the channels between the reservoirs. The device can also include an optical tweezer system to manipulate cells within the microfluidic channels and cell chambers. Optical tweezers combined with microfluidic chips have been described. See e.g., MacDonald et al., *Nature* 426: 421-424, 2003 and Enger et al., Ibid., which are incorporated herein by reference. Optical tweezers can be constructed by directing a laser beam through the objective of a microscope. For example, an optical tweezer can be constructed from an Argon ion pumped titanium-sapphire laser (with a wavelength range of 780 to 850 nm) and a Nikon microscope with a Nikon IR 100× objective with a numerical aperture of 1.3. Individual cells are trapped in the focal point of the laser beam and they can be moved between channels or chambers of a microfluidic device by changing the direction of the laser beam. Alternatively, cells can be sorted in a microfluidic device with an optical tweezer that differentially diverts the flow path of selected cells.

The device can include cell bays ranging in size between approximately 20 µm and 500 µm in diameter can be designed to hold one cell or multiple cells. Channels approximately 10 µm to 200 µm in width can connect the entry ports, cell bays, exit ports and cell traps to create a microfluidic circuit on the device. The quasi-planar substrate includes a fluid or semi-fluid substrate layered over a solid substrate, and the fluid or semi-fluid substrate can contain one or more laterally-mobile ligand molecules and sensors that can move laterally in the plane of the substrate. The fluid substrate can be a membrane, e.g., a phospholipid bilayer, a phospholipid monolayer, or a liquid substrate that is immiscible with the fluids above and below it. Phospholipid bilayers can be comprised of lipids such as phosphatidylcholine, phosphatidylethanolamine, phosphatidylserine, phosphatidic acid, phosphatidylinositol, phosphatidylglycerol, cholesterol and sphingomyelin. For example, phospholipid vesicles can be prepared from cholesterol and L-α-phosphatidylcholine. See, e.g., U.S. Patent Application No. 2005/0208120 published on Sep. 22, 2005 which is incorporated herein by reference. Phospholipid vesicles can be applied to phospholipid bilayer-compatible regions of the device, for example, within cell chambers where they can form a planar phospholipid bilayer surround by fluid layers, i.e., aqueous layers, above and below. See e.g., U.S. Pat. No.

6,228,326 issued to Boxer et al. on May 8, 2001, which is incorporated herein by reference. Phospholipid bilayer vesicles can contain ligands and receptors at least partially embedded in the planar bilayer when the vesicles are applied to a bilayer-compatible surface.

Laterally-mobile ligand molecules and sensors can be embedded in or attached to the fluid or semi-fluid substrate and oriented to bind surface molecules present on the cells of interest above the quasi-planar substrate and to signal via the media below. Ligands can include, but are not limited to, receptor proteins, antibodies, integral membrane proteins, glycophosphatidylinositol-anchored proteins, fusion proteins, conjugated proteins, aptamers or polymers. Sensors can be fixed in place and surrounded by a fluid substrate. Sensors attached to metal electrodes can be layered onto the solid substrate of the device. See e.g., U.S. Pat. No. 6,228,326, Ibid. which is incorporated herein by reference. Sensors can be attached to a metal electrode using alkanethiol linkers. See e.g., Savran et al., *Analytical Chemistry* 76: 3194-3198, 2004, which is incorporated herein by reference. Sensor refers to any device that can detect a measurable quantity. For example, a sensor can be a thermal detector, an electrical detector, a chemical detector, an optical detector, an ion detector, a biological detector, a radioisotope detector, an electrochemical detector, a radiation detector, an acoustic detector, a magnetic detector, a capacitive detector, a pressure detector, an ultrasonic detector, an infrared detector, a microwave motion detector, a radar detector, an electric eye, an image sensor, or a combination thereof. Sensors can use optical detection methods including ellipsometry (see, e.g., Corsel, et al. *J. Colloid Interface Sci* 111: 544-554, 1986, which is incorporated by reference), optical wave guidance (see, e.g., Nellen and Lukosz, *Sensors and Actuators B* 1: 592-596, 1990, which is incorporated herein by reference) or surface plasmon resonance (see, e.g., Cullen, et al. *Biosensors* 3: 211-225, 1988, which is incorporated herein by reference). Surface plasmon resonance is advantageous for monitoring molecular interactions in real-time, enabling a sensitive and comprehensive analysis of the degree of binding interactions between two proteins. On a quasi-planar substrate, a support grid can be fabricated by making an array of conductive regions, e.g., gold, separated by lipid bilayer barrier regions. Biosensors can contain conductive regions, bilayer-compatible regions or bilayer barrier regions, i.e., regions to which lipid bilayers do not adhere. See e.g., U.S. Pat. No. 6,228,326 Ibid., which is incorporated herein by reference. Examples of barrier materials include, but are not limited to: certain polymers, e.g., positive photoresist, metals, e.g., gold, and minerals, e.g., aluminum oxide. A very thin polymer film, such as polyacrylamide or dextran, can be deposited on the conductive regions, e.g., gold, to form bilayer-compatible surface regions. The polyacrylamide can be coupled to a surface by 3-methacryl-oxypropyl-trimethoxy-silane (MPTS; Serva, Heidelberg, Germany). See e.g., Kuhner, et al., *Biophysical Journal* 67: 217-226, 1994, which is incorporated herein by reference. Phospholipid bilayers containing ligand molecules and sensors can be deposited on bilayer-compatible regions as described above. See e.g., U.S. Pat. No. 6,228,326 Ibid., which is incorporated herein by reference. The lipid bilayer-compatible region is located in a cell bay of the device where a solution including cells of interest can be passed over the surface containing the array of receptor-studded lipid expanses. The grid is illuminated at an angle with a light emitting diode (LED), and reflected light is analyzed with a photodetector. An evanescent electric field can be generated by the interaction of incident light with the conductive gold layer. Reflected light from the interaction is sensitive to the environment of a layer extending about 1 µm (approximately 760 nm) from the receptors into the medium. Changes in the environment of the receptor, such as changes caused by binding of a ligand to the receptor, are detected as changes in the reflectance intensity at a specific angle of reflection, termed the resonance angle.

Various cell conditions or cell interactions can be detected on the device by sensors using capacitative detection or impedance analysis. Cell conditions or cell interactions include, but are not limited to, cell engagement, cell binding, cell bay occupancy, ligand binding to a receptor, protein expression, cell product secretion or cell analytes. Cell conditions or cell interactions can be detected by sensors. Capacitative detection or impedance analysis utilizes an electrode incorporated into the bilayer-compatible surface region, and a "ground" electrode placed in the aqueous phase below the bilayer. A voltage from a variable-frequency function generator is used to generate a selected voltage waveform which is fed across selected array elements. The peak-to-peak amplitude of the voltage is typically on the order of about 10 V, but can be substantially less. The voltage is applied over a range of frequencies and the capacitance is determined from the measured current as a function of signal frequency using standard signal processing techniques. The application of capacitance measurements and impedance analyses of supported bilayers are discussed, for example, in Stelzle et al., *Biochim. Biophys. Acta.* 981: 135-142, 1989 which is incorporated herein by reference. Sensor electrodes can be constructed on glass plates onto which chromium layers of approximately 20-50 nm thickness are deposited. The electrode surface can be made hydrophilic by argon sputtering and lipid bilayers can be deposited on the electrode surface and covered by an aqueous solution. Measurement of specific capacitance, specific resistance and electrolyte resistance across the lipid bilayer can be used to detect protein adsorption to the bilayer from the aqueous phase. Cell proteins such as cytokines can be detected by electrodes with lipid bilayers containing specific receptors for the cytokines. Also aptamers can be used as sensors to detect cell surface proteins and cell products such as cytokines Aptamers are small RNA or DNA molecules that specifically bind small molecules, proteins, carbohydrates, and lipids with high specificity and high affinity. Aptamers specific for cell surface antigens and/or cell products can be attached to gold electrodes constructed in a cell chamber using thiol-modified aptamers in solution to react with the gold surface. See e.g., U.S. Pat. No. 6,228,326, Ibid and Savran et al., *Analytical Chemistry* 76: 3194-3198, 2004, which are incorporated by reference herein. Binding of cell surface proteins or cell products to the corresponding aptamers on sensors can transduce an electrical signal that is received by the controller of the device. Cell engagement, cell binding, cell bay occupancy, protein expression, cell activation, cell fertilization, cell product secretion and cell analytes can be detected by sensors and signaled electronically to a controller that can respond to the signals.

Controller refers to any device that can receive, process and present information. For example, a controller can be, e.g., one microprocessor, several microprocessors coupled together, a computer, or several computers coupled together. The controller can have multiple addresses corresponding to each of the sensors in the device. The controller can be programmed to respond appropriately to each of the sensors. For example, a cell engaging a sensor in cell bay 1 can trigger a signal to the controller. The controller, in turn, can respond by opening a valve and actuating a micropump to inject a cytokine into cell bay 1 and by actuating the presentation of ligands and receptors in cell bay 1 designed to interact with the cell. The controller can also respond by causing microfluidic flow in the cell bay to wash the cell or to move the cell to a new location in a second cell bay. By closing and opening piezoelectric gates the device can control a path that the cell takes through the device. The controller can also respond by delivering an electric charge to cell bay 1 to electroporate the cell and to inject one or more gene expression constructs into the cell. The controller can also respond to sensors in cell bay 1 by providing cytokines, ligands, receptors, microfluidic flow or other modifiers to cell bay 2. For example, sensors can detect the activation of a T cell, e.g. by detection of IL-2 production, in cell bay 1 and signal to the controller which can respond by modifying cell bay 2. To capture activated T cells in cell bay 2, the controller can respond by providing membrane-bound antibodies that recognize T cell activation antigens, e.g., anti-HLA-DR and anti-IL-2 receptor α (CD25) in cell bay 2. Phospholipid bilayer vesicles containing membrane bound antibodies (anti-HLA-DR and anti-CD25) can be injected into cell bay 2 to provide a planar lipid bilayer that can capture activated T cells. The controller also can respond by injecting cytokines, e.g., IL-21 and IL-15 into cell bay 2 to promote the survival and maturation of the T cell. See, e.g., Cotner et al., *J. Exp. Med.* 157: 461-472, 1983 and Zeng et al., *J. Exp. Med.* 201: 139-148, 2005 which are incorporated herein by reference.

PROPHETIC EXAMPLES

Example 1

A Micropattern Array Device to Differentiate, Activate and Collect Regulatory T Cells An ex vivo device is constructed to responsively interact with regulatory T (Treg) cells from a patient having auto-immune disease. The device includes a lipid bilayer on a quasi-planar silicon wafer substrate and laterally mobile ligands embedded within the lipid bilayer that interact with receptors on the Treg cells. The device also includes optical sensors and optical waveguide sensors, and a controller that responds to the sensors by delivering effector molecules, e.g., cytokines and receptors to the T cells. The device is constructed using a combination of microelectronic and microfluidic methods to contain single cell chambers connected by channels with gates and collection chambers. The chambers and channels are comprised of multiple layers that include a solid support (silica), an aqueous fluid layer for signal transduction, a lipid bilayer, and a cell fluid media. Treg cells enter the device at an entry port and traverse a microfluidic circuit within the device that activates and collects Treg cells from the patient. The activated Treg cells suppress autoreactive T cells to regulate an autoimmune response to self-antigens in autoimmune disease in the patient.

A device including a micropatterned array is constructed using microfabrication methods to contain single cell compartments composed of multiple layers that include ligands, sensors and controllers that interact responsively to detect, activate and collect Treg cells. Methods are used to create micropattern arrays of lipid bilayers containing membrane proteins. See e.g., U.S. Patent Application No. 2008/0317724 entitled "Micropatterned T Cell Stimulation" published on Dec. 25, 2008 and U.S. Pat. No. 6,228,326 issued to Boxer et al. on May 8, 2001, which are incorporated herein by reference. A patterned support grid is constructed from 100 mm diameter silicon wafers (available from Silrec Corp., San Jose, Calif.). The wafers are maintained at 1000° C. in an oxidation furnace to generate a layer of silicon oxide. Positive photoresist (S-1800 available from Shipley Inc., Marlborough, Mass.) is spin-coated onto the wafers using a track coater (Silicon Valley Group, San Jose, Calif.), and then the wafers are exposed to UV light at approximately 10 mW/cm$^2$ through a photolithographic mask. The micropattern is developed with tetramethylammonium hydroxide developer (Shipley Inc., Marlborough, Mass.), and the wafers are etched for approximately three minutes in argon plasma. The micropattern is designed with single cell chambers approximately 20 µm in diameter connected by channels approximately 10 µm in width that delineate a microfluidic circuit. Single cell chambers are coated with an aqueous layer and a lipid bilayer.

Continuous planar lipid bilayers are formed on the micropattern array using a suspension of phospholipid vesicles containing integral membrane proteins. Phospholipid vesicles are constructed using lipid rafts containing membrane ligands (antibodies or antibody fragments) with specificity for Treg surface markers and activation antigens, CD4, CD25 and CD3.

Antibodies or antibody fragments that act as membrane ligands to recognize Treg surface markers are expressed using recombinant DNA methods in Chinese hamster ovary (CHO) cells. Anti-CD4, anti-CD25 and anti-CD3 membrane proteins are isolated in lipid rafts from the CHO cells expressing the recombinant antibodies or antibody fragments. Recombinant antibodies or antibody fragments that act as membrane ligands are constructed from single chain variable fragments (scFv) fused to a transmembrane domain. Recombinant human antibodies are select from phage display scFv libraries. See e.g., Pansri et al., *BMC Biotechnology* 9(6): 2009; doi: 10.1186/1472-6750-9-6 which is incorporated herein by reference. scFv antibody fragments that recognize CD4, CD25 and CD3 are isolated and engineered to contain a transmembrane domain at the carboxy terminus of each scFv protein. The scFv proteins are constructed as tandem repeats of each scFv. See e.g., Herrmann et al., *Cancer Res.* 68: 1221-1227, 2008, which is incorporated herein by reference. DNA sequences of immunoglobulin are constructed encoding a spacer region, transmembrane domain, and cytoplasmic region from membrane IgM (mIgM). See, e.g., Michnoff et al., *J. Biol. Chem.* 269: 24237-24244, 1994, which is incorporated herein by reference. Complementary DNA (cDNA) encoding scFv specific for CD4, CD25 and CD3 are obtained by molecular cloning using the bacteriophage clones selected above. Methods to isolate mRNA, clone cDNA and determine DNA sequences are provided. See e.g., U.S. Pat. No. 7,141,656 entitled "MHC Complexes and Uses Thereof" issued to Rhodes et al. on Nov. 28, 2006 and Sambrook and Russell, "Molecular Cloning: A Laboratory Manual", Third Edition, 2001, Cold Spring Harbor Laboratory Press, Woodbury, N.Y., which are incorporated herein by reference. A DNA sequence encoding the spacer, transmembrane domain and cytoplasmic tail of mIgM (Genbank Accession No.: AAB59651; amino acids No. 438-475) is fused to the 3' end of each scFv cDNA. The anti-CD3 scFv-mIgM fusion gene and the anti-CD25 scFv-mIgM fusion gene are inserted in a bicistronic mammalian cell expression vector. See e.g., Product Information Sheet: "pIRES Vector" available from Clontech Laboratories, Inc., Mountain View, Calif. which is incorporated herein by reference. A second mammalian cell expression vector encoding the anti-CD4 scFv-mIgM fusion gene is constructed with an alternate selectable marker, e.g., dihydrofolate reductase (DHFR) to allow coselection of the scFv vectors with methotrexate and G418. CHO cells are transfected with one or both scFv-mIgM expression vectors using Lipofectamine™ (available with protocols from Life Technologies Corp., Carlsbad, Calif.). Stable clones are selected for resistance to G418, or methotrexate, or to both drugs. To test for the expression of the scFv-mIgM proteins the cells are stained with fluorescent antibodies (e.g., anti-kappa variable region ($V_k$) antibodies) and analyzed on a flow cytometer. Antibodies, reagents, protocols and flow cytometers are available from BD Biosciences, San Jose, Calif. Stable CHO cell lines expressing anti-CD4 and anti-CD25 and anti-CD3 on the cell surface are expanded in a bioreactor to provide a source of lipid rafts containing anti-CD4, anti-CD25 and anti-CD3 scFv membrane proteins.

To isolate lipid rafts from mammalian cell lines including detergent-free lipid rafts, a carbonate step gradient method is used. See, e.g., Macdonald et al., *J. Lipid Research* 46: 1061-1067, 2005 which is incorporated herein by reference. The cells are washed and scraped into a 500 mM sodium carbonate buffer, pH 11.0, containing 7 different protease inhibitors. The cells are lysed using a Dounce homogenizer and a syringe with a 23 gauge needle and a Branson Sonifier 250. The cell homogenate is fractionated on an OptiPrep™ gradient (available from Axis-Shield PoC, Oslo, Norway) and fractions containing lipid rafts are identified by immunoblotting with antibodies specific for membrane proteins (e.g., anti-CD4, anti-CD25 and anti-CD3 scFv).

Phospholipid vesicles are prepared from cholesterol and L-α-phosphatidylcholine. See, e.g., U.S. Patent Application No. 2005/0208120 published on Sep. 22, 2005, which is incorporated herein by reference. Cholesterol and L-α-phosphatidyl choline are combined at a molar ratio of 2:7 in chloroform. The chloroform is evaporated away using an argon stream. The vesicles are resuspended in a 140 mM NaCl, 10 mM Tris HCl, 0.5% deoxycholate at pH 8 and sonicated for three minutes. Lipid rafts containing scFv specific for Treg markers (e.g., CD4, CD25, and CD3) are inserted in the vesicles by combining the lipid rafts containing anti-CD4, anti-CD25 and anti-CD3 scFv with the phospholipid vesicles at a 1:10 molar ratio and dialyzing for 72 hours at 4° C. versus phosphate-buffered saline. The vesicles are characterized to assess vesicle size and the amount of anti-CD4, anti-CD25 and anti-CD3 scFv protein incorporated in the vesicles. Vesicle size is determined using dynamic light scattering and flow cytometry (see e.g., U.S. Patent Application No. 2005/0208120, Ibid.). For example, vesicles with a mean diameter of approximately 25 nanometers are optimal. To quantify scFv protein on the vesicles, the vesicles are analyzed on a flow cytometer after staining with FITC-labeled anti-$V_k$ antibody. Vesicles are sorted based on FITC fluorescence, forward scatter and side scatter to isolate and count vesicles with scFv. Surface scFv protein on the vesicles is quantified using an enzyme-linked immunosorbent assay (ELISA). Methods to analyze vesicles by flow cytometry and to quantify scFv and other proteins by ELISA are provided. See e.g., U.S. Patent Application No. 2005/0208120, which is incorporated herein by reference.

Phospholipid bilayers are formed on the micropattern arrays by contacting the patterned surface of the wafer support grids with a suspension, prepared as described above, containing approximately 25 nm diameter vesicles. Vesicles in the suspension spontaneously assemble to form a continuous single bilayer on the bilayer-compatible regions of the support grid. Regions of the grid where photoresist remains are not bilayer compatible and form barrier regions or boundaries around the lipid bilayer. Methods to construct bilayer compatible regions and barrier regions are provided. See, e.g., U.S. Pat. No. 6,228,326, which is incorporated herein by reference.

To construct a differentiation and activation path for Treg cells, two single cell compartments (bays) connected by microfluidic channels are coated with vesicles containing different scFv. Cell bay 1 is coated with anti-CD4 scFv vesicles; cell bay 2 is coated with anti-CD25 plus anti-CD3 vesicles. A channel exits from cell bay 2 and connects to a cell collection trap where activated Treg cells are recovered. Microfluidic cell traps are provided. See e.g., Liu et al., *Lab Chip* 9: 1200-1205, 2009, which is incorporated herein by reference. Methods to construct microfluidic channels, on-chip pumps, piezoelectric actuators, valves and reservoirs in microchips are described. See e.g., U.S. Pat. No. 7,435,578 issued to Wikswo et al. on Oct. 14, 2008 which is incorporated herein by reference. Microchips are constructed to maintain controlled temperature (approximately 37° C.) and 5% $CO_2$ atmosphere to promote mammalian cell growth.

The device including the micropatterned array is constructed with optical sensors located underneath the lipid bilayer coating the single cell bays. Methods to construct microchips with optical sensors are provided. See, e.g., Nellen and Lukosz, *Sensors and Actuators B* 1: 592-596, 1990; U.S. Pat. No. 7,435,578 Ibid. and U.S. Patent Application No. 2004/0219605 by Finkel et al. published on Nov. 4, 2004, which are incorporated herein by reference. The device incorporates a fiber-coupled optical system that includes an optical waveguide sensor (available from Micro-Vacuum Ltd., Budapest, Hungary; see e.g., OWLS Application Notes NO-004, "Quantification of Cell Adhesivity" which is incorporated herein by reference). A laser light source is integrated into the cell bay to irradiate the lipid bilayer and the waveguide sensor. Optical signals are conveyed through the waveguide to attached optical fibers and finally to a potentiometric light detector. For example, a CD4-positive T cell binds to anti-CD4 scFv presented on the surface of bay 1 and alters the optical signal emanating from the waveguide sensor. The altered optical signal is detected by the potentiometric light detector and relayed to a controller where a response is initiated. Optical sensors immediately below the lipid bilayers in the cell bays containing anti-CD4, anti-CD25, and anti-CD3 scFv detect when a cell engages, i.e., binds, the scFv and occupies or leaves the cell bay. The controller contains microcircuitry and programs to respond when cells are located in bay 1 or bay 2. For example, CD4+ T cells detected in bay 1 are provided with transforming growth factor β (TGF-β) to promote the development of Treg cells. See e.g., Bettelli et al., *Nature* 441: 235-238, 2006 which is incorporated herein by reference.

After CD4$^+$ T cells are exposed to human TGF-β1 (at approximately 3 ng/mL) for approximately 3 days, the treated cells are moved by pumping fluid via a channel to bay 2 for activation. Individual Treg cells expressing CD25 and CD3 are captured in cell bay 2 by anti-CD25 and anti-CD3 scFv recognizing each antigen. The CD25$^+$, CD3$^+$ Treg cells are detected by optical sensors as described above. Controllers respond to the CD25$^+$, CD3$^+$ Treg cells docked in bay 2 by provision of interleukin 2 (IL-2) at 20 IU/mL to the cells. The IL-2-treated T cells are incubated approximately 72 hours. The differentiated and activated Treg cells are moved by fluid flow to a cell collection trap to be harvested or infused directly into the patient to treat autoimmune disease.

Example 2

A Method to Treat a Patient with Autoimmune Disease by Ex Vivo Leukapheresis and Activation and Collection and Reinfusion of Antigen Specific (Autoreactive Suppressors) Treg Cells A patient with relapsing-remitting multiple sclerosis (MS) is treated with an ex vivo device that differentiates, activates and collects regulatory T (Treg) cells for immune cell therapy. Treg cells suppress autoreactive T cells associated with multiple sclerosis in a patient. See e.g., Yu et al., *J. Immunol.* 174: 6772-6780, 2005 which is incorporated herein by reference. The activated Treg cells are reinfused into the patient to reduce or eliminate the autoimmune attack on the central nervous system associated with MS. T cells are obtained from the peripheral blood of the MS patient, and potential Treg cells are isolated using leukapheresis methods. See e.g., Hoffmann et al., *Blood* 104: 895-903, 2004 which is incorporated herein by reference. Treg cells are processed in a micropattern array device that responsively interacts with the Treg cells to differentiate, activate and collect the cells prior to reinfusion into the patient.

Potential Treg cells are isolated from a MS patient by using immune-magnetic beads and fluorescence activated cell sorting of the blood of the patient. Peripheral blood mononuclear cells (PBMNC) are isolated from the peripheral blood of the patient using a leukapheresis procedure and density gradient separation over Ficoll/Hypaque (available from Sigma-Aldrich Chem. Co., St. Louis, Mo.). The leukocytes are stained with a phycoerythrin (PE)-conjugated anti-CD25 antibody and anti-PE magnetic beads (available from Miltenyi Biotec, Bergisch Gladbach, Germany). $CD25^+$ cells are enriched with the use of a Midi-MACS™ cell separator system (Miltenyi Biotec). $CD25^+$ cells are stained with fluorescein isothiocyanate (FITC)-conjugated anti-CD4 antibodies and sorted using a FACStar™ Plus flow cytometer (from BD Biosciences, San Jose, Calif.) to isolate a $CD4^+CD25^{hi}$ population of potential Treg cells (see e.g., Hoffmann et al., 2004, Ibid.). By FACS sorting, approximately 1.8% of PBMNC are recovered as $CD4^+CD25^{hi}$ cells with a purity of 98%. Leukapheresis can yield $10^{10}$ cells from a single procedure thus yielding maximally about $1.8 \times 10^8$ potential Treg cells for differentiation, activation, and infusion.

A device including a micropattern array with multiple parallel paths for Treg cells is used to differentiate and activate potential Treg cells (i.e., $CD4^+CD25^{hi}$ cells). Each path or circuit includes two single cell compartments (bays) coated with lipid bilayers containing different antibodies, anti-CD4, anti-CD25, or anti-CD3 scFv antibodies, and connected by microfluidic channels. Channel exits from cell bay 2 connect to a cell collection trap where activated Treg cells are recovered. Microfluidic cell traps are provided. See, e.g., Liu et al., *Lab Chip* 9: 1200-1205, 2009 which is incorporated herein by reference. Cell bay 1 is coated with an anti-CD4 scFv in lipid bilayer membrane; cell bay 2 is coated with an anti-CD25 scFv plus anti-CD3 scFv in lipid bilayer membrane. Potential Treg cells suspended in media (e.g., RPMI 1640 with 10% human serum albumin) enter the path through an entry valve and channel in the device and arrive, in succession at bay 1, at bay 2, and at the collection trap. The micropatterned array is also constructed with optical sensors located underneath the lipid bilayer coating the single cell bays. The device incorporates a fiber-coupled optical system that includes an optical waveguide sensor, available from MicroVacuum Ltd., Budapest, Hungary; see e.g., OWLS Application Notes NO-004, "Quantification of Cell Adhesivity" which is incorporated herein by reference. A laser light source is integrated into the cell bay to irradiate the lipid bilayer and the waveguide sensor. Optical signals are conveyed through the waveguide to attached optical fibers and then to a potentiometric light detector. For example, a $CD4^+$ T cell binds to anti-CD4 scFv presented on the surface of bay 1 and alters the optical signal emanating from the waveguide sensor. The altered optical signal is detected by the potentiometric light detector and relayed to a controller where a response is initiated. Optical sensors immediately below the lipid bilayers in the cell bays containing scFv (anti-CD4, anti-CD25 or anti-CD3) detect when a cell engages (i.e., binds) the scFv and occupies or leaves the cell bay. A controller contains microcircuitry and programs to respond to optical signals emanating from a specific path and single cell bay. For example, $CD4^+$ T cells detected in path 1, bay 1 are provided with transforming growth factor β (TGF-β) to promote the development of Treg cells. See e.g., Bettelli et al., *Nature* 441: 235-238, 2006 which is incorporated herein by reference.

After $CD4^+$ T cells are exposed to human TGF-β (at approximately 3 ng/mL) for approximately 3 days, the activated $CD4^+$ T cells are moved to bay 2 for activation by pumping fluid via a channel between bay 1 and bay 2. Individual Treg cells expressing CD25 and CD3 are captured in cell bay 2 by anti-CD25 scFv and anti-CD3 scFv recognizing each antigen. The Treg cells are detected by optical sensors as described above. Controllers respond to the $CD25^+$, $CD3^+$ Treg cells docked in bay 2 are exposed to interleukin 2 (IL-2) at 20 IU/mL and incubated approximately 72 hours. See e.g., Bollyky et al., *J. Immunol.* 183: 2232-2241, 2009 which is incorporated herein by reference. Finally the differentiated and activated Treg cells are moved by fluid flow to a cell collection trap to be harvested or infused directly.

Treating a MS patient by reinfusion of activated, polyclonal, autologous Treg cells obtained from the micropattern device can suppress autoreactive T cells that are associated with the disease and reduce or eliminate the neurodegeneration associated with MS.

Example 3

A Device to Differentiate Peripheral Blood Dendritic Precursor Cells to Activated, Mature Dendritic Cells and Load them with Viral Antigens A device including a micropattern array is constructed to differentiate and activate antigen presenting cells (APC) and load antigen onto the APCs. The device is constructed as a microfluidic chip on a quasi-planar substrate having one or more laterally-mobile effector molecule types at least partially embedded within the quasi-planar substrate, including a fluid circuit comprised of interconnected channels and single cell bays that responsively interact with the APC. Activated, antigen-loaded APC are used for immunotherapy and for immunology research.

The device including the micropattern array is constructed with channels, single cell bays, sensors, controllers, ligands, antigens and cytokines that are incorporated in a microfluidic chip. Methods to construct microfluidic chips are provided. See, e.g., Liu et al., *Lab Chip* 9: 1200-1205, 2009 which is incorporated herein by reference. A microfluidic chip is constructed from polydimethylsiloxane (PDMS) using a "liquid-molding" procedure to create interconnected channels, single cell bays, reservoirs and cell collection traps for APC processing. Glass slides (25 mm×75 mm) are used to create wetting/dewetting patterned surfaces. The slide is silanized (to render it hydrophobic) with 3-(trimethoxysilyl) propyl methacrylate (3% v/v) and baked at 120° C. for 4 hours, thus forming free methacrylate groups on the surface. Photolithography is used to fabricate micropatterns of hydrophilic regions (polymerized acrylamide) on the slide. The slide is dipped in a polar glycerol solution to create a micropattern of glycerol adhering only to the hydrophilic regions. PDMS solution (Dow Corning, Midland, Mich.) is poured onto the glycerol micropattern to a depth of approximately 5 mm and cured at 60° C. for 1 hour. The PDMS substrate with a replicate channel structure is lifted off of the glycerol mold and drilled to create access holes, install pumps, valves and gates. Phospholipid bilayers, ligands, sensors and electrodes are added to the cell bays, and lastly the PDMS substrate is bonded onto a glass slide with 1 minute treatment with oxygen plasma. Channels with a width of approximately 500 µm and an apical height of approximately 50 µm are created connecting cell chambers, reservoirs, cell collection traps and external ports. Approximately 75-150 parallel microfluidic circuits can be created in a 25 mm×75 mm microchip (see e.g., Liu et al., Ibid.). Methods to construct microfluidic channels, on-chip pumps, piezoelectric actuators, valves and reservoirs in microchips are described (see e.g., U.S. Pat. No. 7,435,578 issued to Wikswo et al. on Oct. 14, 2008 which is incorporated herein by reference). Moreover methods to install gold electrodes and associated circuitry in microdevices are provided. See, e.g., U.S. Pat. No. 6,228,326 issued to Boxer et al. on May 8, 2001 which is incorporated herein by reference. The microdevice is constructed with heating elements and thermocouple devices to maintain a controlled temperature (approximately 37° C.) to promote mammalian cell differentiation and survival. The microchip cell bays are coated with a quasi-planar substrate, a phospholipid bilayer that contains embedded ligands, receptors and sensors that responsively interact with the APC as they travel a microfluidic circuit.

The device including the micropattern array contains multiple (approximately 75) parallel micro-circuits that engage, differentiate, activate and load dendritic cells (DC) with antigen. Methods to derive dendritic cells (DC) from peripheral blood mononuclear cells (PBMNC) are provided. See, e.g., Krug et al., Eur. J. Immunol. 31: 3026-3027, 2001 and Gilboa, J. Clin. Invest. 117: 1195-1203, 2007, which are incorporated herein by reference). Each micro-circuit includes an entry channel leading to cell bay 1, an exit channel leading to cell bay 2, and an exit channel leading to a cell collection trap. Cell bay 1 contains: surface-bound CD1c sensors; a granulocyte macrophage colony stimulating factor (GMCSF) injector; surface bound CD304 sensors; a cytosine-guanosine (CpG)-rich oligodeoxynucleotide (ODN) injector; an injector for a tumor associated antigen, prostate acid phosphatase (PAP); CD40 sensors; and CD80 sensors. Cell bay 2 contains: membrane bound anti-CD54 (ICAM-1) scFv and anti-HLA-DR scFv. Cell bays are constructed with a lipid bilayer containing embedded membrane proteins and gold electrode regions bearing aptamer-based sensors. See e.g., Lai et al., Anal. Chem. 79: 229-233, 2007 which is incorporated herein by reference.

Membrane ligands that recognize dendritic cell surface markers are expressed using recombinant DNA methods in Chinese hamster ovary (CHO) cells and isolated within lipid rafts. Some membrane ligands are constructed from single chain variable fragments (scFv) fused to a transmembrane domain. Methods to select human antibody fragments from phage display scFv libraries are provided. See, e.g., Pansri et al., BMC Biotechnology 9(6): 2009; doi: 10.1186/1472-6750-9-6, which is incorporated herein by reference. Single chain variable fragments that recognize CD54 and HLA-DR are isolated and engineered to contain a transmembrane domain at the carboxy terminus of each scFv protein. The scFv proteins are constructed as tandem repeats of each scFv. See e.g., Herrmann et al., Cancer Res. 68: 1221-1227, 2008 which is incorporated herein by reference. DNA sequences of immunoglobulin (Ig) constructs encoding a spacer region, transmembrane domain, and cytoplasmic region from membrane IgM (mIgM) are provided. See, e.g., Michnoff et al., J. Biol. Chem. 269: 24237-24244, 1994 which is incorporated herein by reference. Complementary DNA (cDNA) encoding anti-CD54 scFv and anti-HLA-DR scFv are obtained by molecular cloning using the bacteriophage clones selected from scFv libraries (see above). Methods to clone genes and cDNA and to determine DNA sequences are provided. See, e.g., U.S. Pat. No. 7,141,656 entitled "MHC Complexes and Uses Thereof" issued to Rhodes et al. on Nov. 28, 2006 and Sambrook and Russell, "Molecular Cloning: A Laboratory Manual", Third Edition, 2001, Cold Spring Harbor Laboratory Press, Woodbury, N.Y., which are incorporated herein by reference. A DNA sequence encoding the spacer, transmembrane domain and cytoplasmic tail of mIgM (Genbank Accession No.: AAB59651; amino acids No. 438-475) is fused to the 3' end of each scFv cDNA. The anti-CD54 scFv-mIgM fusion gene and the anti-HLA-DR scFv-mIgM fusion gene are inserted in a bicistronic mammalian cell expression vector. See, e.g., Product Information Sheet: "pIRES Vector" available from Clontech Laboratories, Inc., Mountain View, Calif. which is incorporated herein by reference. Chinese hamster ovary (CHO) cells are transfected with the expression vector encoding anti-CD54 scFv and the expression vector encoding anti-HLA-DR scFv using Lipofectamine™ transfection reagent (available with protocols from Life Technologies Corp., Carlsbad, Calif.). Stable clones are selected for their resistance to G418. To test for the expression of the scFv-mIgM proteins, the cells are stained with fluorescent antibodies, e.g., anti-kappa variable region ($V_k$) antibodies and analyzed on a flow cytometer. Antibodies, reagents, protocols and flow cytometers are available from BD Biosciences, San Jose, Calif. Stable CHO cell lines expressing anti-CD54 scFv and anti-HLA-DR scFv on their cell surfaces are expanded in a bioreactor to provide a source of lipid rafts containing the corresponding membrane proteins.

Methods to isolate lipid rafts from mammalian cell lines are provided. See, e.g., Macdonald et al., J. Lipid Research 46: 1061-1067, 2005 which is incorporated herein by reference. Detergent-free lipid rafts are prepared using a carbonate step gradient method. The cells are washed and scraped into a 500 mM sodium carbonate buffer, pH 11.0, containing 7 different protease inhibitors. The cells are lysed using a Dounce homogenizer, a syringe with a 23 gauge needle, and a Branson Sonifier 250. The cell homogenate is fractionated on an OptiPrep™ gradient (available from Axis-Shield PoC, Oslo, Norway) and fractions containing lipid rafts are identified by immunoblotting with antibodies specific for membrane proteins (e.g., scFv, CD40 ligand; protocols and antibodies from BD Biosciences, San Jose, Calif.).

Phospholipid vesicles are prepared from cholesterol and L-α-phosphatidylcholine. See, e.g., U.S. Patent Application No. 2005/0208120 published on Sep. 22, 2005). Cholesterol and L-α-phosphatidyl choline are combined at a molar ratio of 2:7 in chloroform and the chloroform is evaporated away using an argon stream. The vesicles are resuspended in a 140 mM NaCl, 10 mM Tris HCl, 0.5% deoxycholate at pH 8 and sonicated for three minutes. Lipid rafts containing membrane proteins (anti-CD54 scFv and anti-HLA-DR scFv) specific for dendritic cell activation receptors (e.g., CD54 and HLA-DR) are inserted in the vesicles by combining the lipid rafts containing the membrane proteins with the phospholipid vesicles at a 1:10 molar ratio and dialyzing for 72 hours at 4° C. versus phosphate-buffered saline. The vesicles are characterized to assess vesicle size and the amount of membrane protein incorporated in the vesicles. Vesicle size is determined using dynamic light scattering and flow cytometry (see e.g., U.S. Patent Application No. 2005/0208120, Ibid.). For example, vesicles with a mean diameter of approximately 25 nanometers are optimal. To quantify scFv protein on the vesicles the vesicles are analyzed on a flow cytometer after staining with FITC-labeled anti-$V_k$ antibody. Vesicles are sorted based on fluorescence, forward scatter and side scatter to isolate and count vesicles presenting scFv. Surface scFv protein on the vesicles is also quantified using an enzyme-linked immunosorbent assay (ELISA). Methods to analyze vesicles by flow cytometry and to quantify scFv and other proteins by ELISA are provided. See, e.g., U.S. Patent Application No. 2005/0208120, Ibid.

Phospholipid bilayers are formed on cell bay 1 and cell bay 2 by contacting the PDMS microchip with a suspension, prepared as described above, containing approximately 25 nm diameter vesicles. Vesicles in the suspension spontaneously assemble to form a continuous single lipid bilayer on the lipid bilayer-compatible regions of the microfluidic chips. Regions of the microchip that are not lipid bilayer compatible do not retain a lipid bilayer. Methods to construct lipid bilayer compatible regions and barrier regions are provided. See, e.g., U.S. Pat. No. 6,228,326 Ibid. CPG oligodeoxynucleotides are added to the phospholipid bilayer present in cell bay 1 to stimulate dendritic cells via their Toll-like receptors (TLR). CPG-ODN (available from InvivoGen, San Diego, Calif.) is condensed with a polycationic polymer, polyethyleneimine and injected onto the lipid bilayer coating bay 1. Positively charged, condensed CpG oligonucleotides bind to the negatively charged phospholipid bilayer. See e.g., Ali et al., *Sci. Transl. Med.* 1: 8ra19, 2009 which is incorporated by reference.

The micropattern device also contains sensors to detect the engagement and activation of dendritic cells. Methods to make aptamer-based sensors that send an electronic signal are provided. See, e.g., Lai et al., *Anal. Chem.* 79: 229-233, 2007 which is incorporated herein by reference). Aptamers are small RNA or DNA molecules that specifically bind small molecules, proteins, carbohydrates, and lipids with high specificity and high affinity. Aptamers that recognize a specific target are obtained by in vitro selection from a library of oligodeoxynucleotides with random sequences (see Lee et al., *Anal. Bioanal. Chem.* 390, 1023-1032 (2008) which is incorporated herein by reference). Sensors to detect CD304, CD1c, CD40 or CD80 are constructed from aptamers selected to recognize recombinant CD304, CD1c, CD40 and CD80 protein (CD40 and CD80 proteins available from Abnova, Walnut, Calif.; CD304 protein available from R&D Systems, Minneapolis, Minn.). Aptamers specific for CD304, CD1c, CD40 and CD80 are attached to gold electrodes constructed in cell bay 1 (see e.g., U.S. Pat. No. 6,228,326, Ibid.) using thiol-modified aptamers in solution to react with the gold surface. See e.g., U.S. Pat. No. 6,228,326, Ibid. For example, a DNA aptamer, 51 nucleotides long derivatized with a C6 thiol linker ($HS(CH_2)_6PO_4$) at its 5' end can be immobilized on a gold-coated surface by incubation of a 10 μM aptamer solution with the gold surface for approximately 20 minutes. See, Savran et al., *Analytical Chemistry* 76: 3194-3198, 2004 which is incorporated by reference herein. Binding of cell surface proteins, CD304, CD1c, CD40 and CD80 to the corresponding aptamers on sensors transduces an electrical signal that is relayed to the controller of the microfluidic device. The controller in turn actuates pumps and valves to responsively interact with the APC. For example, binding of a myeloid dendritic cell to the CD1c sensor in bay 1 signals the controller to actuate a pump and valve to inject GMCSF (at approximately 10 μg/ml) and prostatic acid phosphatase antigen to cell bay 1 to promote differentiation, activation and antigen loading of the engaged dendritic cells. See Small et al., *J. Clin. Oncol.* 18: 3894-3903, 2000 which is incorporated herein by reference. Activation of the dendritic cells in cell bay 1 is accompanied by increased CD80 and CD40 expression on the cell surface. Aptamer sensors in bay 1 bind to CD80 and CD40 and signal the controller that an activated dendritic cell is engaged in bay 1. The controller responds by enabling hydrofluidic flow to move the activated dendritic cell to cell bay 2. Activated dendritic cells are retained in bay 2 by binding to membrane bound anti-HLA-DR scFv and anti-CD54 scFv. Unactivated dendritic cells are not retained in bay 2 and routed to a waste reservoir. After a few minutes of fluid flow to move the dendritic cells from bay 1, a piezoelectric gate is opened to route the activated dendritic cells to a cell collection trap, and cell bay 2 is flooded with media emanating from a micropump and valve to drive activated dendritic cells to a cell trap. Activated, antigen-loaded, APC are harvested from the cell trap and characterized. Activated, antigen-loaded APC are used for immunotherapy in patients and for immunology research.

Example 4

A Method to Treat a Patient with Prostate Cancer Using a Micropattern Cell Treatment Array Ex Vivo to Vaccinate the Patient with Dendritic Cells and Prostate Cancer Antigens A patient with hormone refractory prostate cancer is treated with immune cells derived from an ex vivo device including a micropattern array that differentiates, activates, loads and collects antigen presenting cells (APC) for immune cell therapy. Dendritic cell (DC) precursors are obtained from the patient's peripheral blood and they are processed in a device including the micropattern array that responsively interacts with the cells to differentiate, activate, load and select them prior to reinfusion in the patient. Immunotherapy for prostate cancer with antigen-loaded dendritic cells is provided. See, e.g., Small et al., *J. Clin. Oncol.* 18: 3894-3903, 2000 and Gilboa, *J. Clin. Invest.* 117: 1195-1203, 2007, which are incorporated herein by reference.

The patient has a prostatic acid phosphatase (PAP) level in his serum that is greater than or equal to 2 times the upper limit of normal PAP (3.0 ng/mL) and has histologically confirmed adenocarcinoma of the prostate. To obtain dendritic cell precursors, the patient's peripheral blood mononuclear cells (PBMNC) are collected by leukapheresis followed by density gradient centrifugation. See e.g., Small et al., Ibid. Dendritic cells are isolated from the PBMNC by methods as provided. See, e.g., Product Data Sheet: "Blood Dendritic Cell Isolation Kit II" available from Miltenyi Biotec Inc., Auburn, Calif. which is incorporated herein by reference. PBMNC are subjected to depletion to remove B cells and monocytes followed by positive selection with magnetic beads that recognize plasmacytoid DC and myeloid DC (i.e., conventional DC). Purified DC populations (approximately 90-98% pure) represent about 1% of total PBMNC. Purified DC precursor cells are injected into an entry port of a micropattern array device that distributes the cells to multiple parallel microcircuits which responsively interact with the dendritic cell precursors to generate mature, antigen-loaded dendritic cells for reinfusion into the patient with prostate cancer.

The device including the micropattern array contains multiple (approximately 75) parallel micro-circuits that engage, differentiate, activate and load dendritic cells with antigen. Methods to isolate dendritic precursor cells from peripheral blood mononuclear cells (PBMNC) are provided. See, e.g., Angelot et al., *Haematologica* 94: 1502-1512, 2009 which is incorporated herein by reference. Each microcircuit includes an entry channel leading to cell bay 1, an exit channel leading to entry to cell bay 2, and an exit channel leading to a cell collection trap. Cell bay 1 contains: surface-bound CD1c sensors; a granulocyte macrophage colony stimulating factor (GMCSF) injector; surface bound CD304 sensors; a cytosine-guanosine (CpG)-rich oligodeoxynucleotide (ODN) injector; an injector for a tumor-associated antigen, prostate acid phosphatase (PAP); CD40 sensors; and CD80 sensors. Cell bay 2 contains: membrane bound anti-CD304 scFv, membrane bound anti-CD1c scFv, and membrane bound CD40 ligand. Cell bays are constructed with a lipid bilayer containing embedded membrane proteins and gold electrode regions bearing aptamer-based sensors. See e.g., Lai et al., *Anal. Chem.* 79: 229-233, 2007 which is incorporated herein by reference.

Dendritic precursor cells, that express CD1c (myeloid DC) or CD304 (plasmacytoid DC) flow into cell bay 1 and bind to the CD1c sensor or CD304 sensor, respectively. Following myeloid DC binding to the CD1c sensor, the sensor signals the controller to actuate a pump and valve that provide GMCSF at approximately 10 µg/ml and PAP antigen at approximately 10 µg/mL to cell bay 1 to promote differentiation, activation and loading of engaged myeloid DC. Upon plasmacytoid DC binding to the CD304 sensor a signal to the controller leads to actuation of a pump and valve that dispense CPG-ODN and PAP antigen. Activation and maturation of the dendritic cells in cell bay 1, indicated by CD80 and/or CD40 expression, is detected by the corresponding aptamer sensors. Signaling from the CD40 or CD80 sensors in bay 1 to the controller results in actuating a micro-pump to pump fluid into bay 1 and opening an exit valve to allow the activated DC to flow into bay 2 of the device. Activated DC are retained in bay 2 by binding to CD40 ligand while unactivated DC are not retained in bay 2 and routed to a waste reservoir. After a few minutes of fluid flow to move the DC from bay 1, a piezoelectric gate is opened to route the activated DC to a cell collection trap. Cell bay 2 is flooded with media emanating from a micropump and valve to drive activated DC to the cell trap. The DC are harvested from the cell trap and characterized prior to reinfusion in the patient.

Activated DC processed in the device including the micropattern array are analyzed to verify that they are safe and effective APC for treatment of prostate cancer in the patient. Methods to characterize APC for infusion are provided. See, e.g., Small et al., Ibid.). A sterility test of the cell preparation is done by checking for microbial growth after 40 hours in nutrient broth at 37° C. Endotoxin tests (criterion is less than 1.4 EU/ml) and mycoplasma testing are done. The activated DC are phenotyped by flow cytometry to assess maturation and activation. DC are stained with fluorescent antibodies (Ab) specific for: CD304, CD1c, HLA-DR, CD80, CD86 and CD40. CD304 and CD1c Ab are available from Miltenyi Biotec Inc., Auburn, Calif.; HLA-DR, CD80, CD86 and CD40 Ab are available from BD Biosciences, San Jose, Calif. Criteria for identification of mature, activated DC are described. See e.g., Angelot et al., Ibid.

To evaluate the immune function of the processed DC, the activated DC are tested for their ability to stimulate allogeneic and autologous T cells in a proliferation assay. Assays to test human DC in mixed lymphocyte reactions are provided. See, e.g., Small et al., Ibid. Human T cells are isolated from the PBMNC of allogeneic donors or from the patient (autologous) using CD3 T cell enrichment columns to provide allogeneic or autologous responder cells. Isolated DC precursor cells (pre-processing) or activated DC (post-processing) are compared in cultures including tritiated thymidine to monitor T cell proliferation in culture. For both allogeneic and autologous T cells, activated DC (post-processing) stimulate 4-5 times the T cell proliferation stimulated by precursor DC (pre-processing).

Activated, mature DC loaded with PAP and tested for safety and immune function are formulated in lactated Ringers' solution and stored at 4° C. until they are infused in the patient with prostate cancer. Approximately $0.2 \times 10^8$ to $2.0 \times 10^8$ activated DC/m$^2$ are infused in total volume of 250 mL at 0, 4 and 8 weeks. Proliferation of the tumor is monitored in the patient, and additional infusions of activated mature DC loaded with PAP can be prepared using the device including the micropattern array starting with frozen PBMNC from the patient or freshly harvested PBMNC.

Each recited range includes all combinations and subcombinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

The state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Optical aspects of implementations will typically employ optically-oriented hardware, software, and/or firmware.

In a general sense the various aspects described herein which can be implemented, individually and/or collectively, by a wide range of hardware, software, firmware, or any combination thereof can be viewed as being composed of various types of "electrical circuitry." "Electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the description accompanying them are used as examples for the sake of conceptual clarity and that various configuration modifications using the disclosure provided herein are within the skill of those in the art. Consequently, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. A system comprising
   a fluid bypass configured to passage fluids including one or more cell types from a vertebrate subject into a device and configured to return the passaged fluids to the vertebrate subject, wherein the device includes a quasi-planar substrate; and two or more laterally-mobile effector molecule types at least partially embedded within the quasi-planar substrate, wherein the two or more laterally-mobile effector molecule types are sequentially placed and configured to interact with one or more cell types;

one or more sensors configured to detect the at least one aspect of the interaction between the two or more laterally-mobile effector molecule types and the one or more cell types; and a controller in communication with the one or more sensors, wherein the controller is configured to responsively initiate modification of at least one of the two or more laterally-mobile effector molecule types, the quasi-planar substrate, or the one or more cell types sufficient to initiate activation, maturation, differentiation, anergy induction, antigen loading, binding, electroporation, or transduction in the one or more cell types.

2. The system of claim 1, wherein at least one of the two or more effector molecule type is a ligand molecule.

3. The system of claim 1, wherein at least one of the two or more effector molecule type is a receptor molecule.

4. The system of claim 1, wherein at least one of the two or more effector molecule type is a cytokine.

5. The system of claim 1, wherein at least one of the two or more laterally-mobile effector molecule types modified in response to the controller is different from at least one of the two or more laterally-mobile effector molecule types sensed interacting with the one or more cell types by the one or more sensors.

6. The system of claim 1, wherein the controller is configured to responsively add at least one of the two or more laterally-mobile effector molecule types to the quasi-planar substrate.

7. The system of claim 1, wherein the quasi-planar substrate includes one or more discreet regions configured to include at least one of the two or more laterally-mobile effector molecule types.

8. The system of claim 1, wherein the controller is configured to responsively remove at least one of the two or more laterally-mobile effector molecule types from the quasi-planar substrate.

9. The system of claim 1, wherein the controller is configured to responsively move at least one of the two or more laterally-mobile effector molecule types and the one or more cell types relative to the quasi-planar substrate.

10. The system of claim 1, wherein the controller is configured to responsively remove at least one of the two or more laterally-mobile effector molecule types and the one or more cell types from the quasi-planar substrate.

11. The system of claim 1, wherein the quasi-planar substrate includes a liquid configured as an interface with a cell type-carrying fluid.

12. The system of claim 11, wherein the liquid is configured to at least partially embed the two or more laterally-mobile effector molecule types on the quasi-planar substrate.

13. The system of claim 11, wherein the quasi-planar substrate includes a membrane.

14. The system of claim 13, wherein the membrane is bordered by a solid substrate.

15. The system of claim 13, wherein the membrane includes a lipid bilayer.

16. The system of claim 11, wherein the cell type-carrying fluid includes a gas or a liquid.

17. The system of claim 1, wherein the quasi-planar substrate includes a solid surface configured to at least partially embed at least one of the two or more laterally-mobile effector molecule types.

18. The system of claim 17, wherein the quasi-planar substrate includes a liquid at least partially surrounding the solid surface, wherein the liquid is configured to at least partially embed at least one of the two or more laterally-mobile effector molecule types within the liquid.

19. The system of claim 1, wherein the quasi-planar substrate is configured to mobilize at least one of the two or more laterally-mobile effector molecule types in essentially two dimensions on the quasi-planar substrate.

20. The system of claim 1, wherein the quasi-planar substrate is configured to bi-directionally mobilize at least one of the two or more laterally-mobile effector molecule types in essentially one dimension on the quasi-planar substrate.

21. The system of claim 1, wherein the quasi-planar substrate is configured to include one or more spatially-discrete portions connected by a fluidic interface.

22. The system of claim 21, wherein the controller includes one or more of static connections or dynamic connections, wherein the one or more of the static connections or the dynamic connections are configured to control communication between the one or more spatially discrete portions.

23. The system of claim 1, wherein at least one of the two or more laterally-mobile effector molecule types is configured to undergo a conformational change in response to interaction with the one or more cell types.

24. The system of claim 1, wherein at least one of the two or more laterally-mobile effector molecule types is configured to react with one or more binding components in response to interaction with the one or more cell types.

25. The system of claim 24, wherein the one or more binding components is laterally mobile in the substrate.

26. The system of claim 24, wherein the one or more binding components is on the one or more cell types.

27. The system of claim 1, wherein at least one of the two or more laterally-mobile effector molecule types is configured to bind and interact with a single cell type of the one or more cell types.

28. The system of claim 27, wherein the sensor is configured to identify the single cell type, and the controller is configured to modify the single cell type.

29. The system of claim 1, wherein the one or more sensors is configured to spatially detect at least one of the one or more laterally-mobile effector molecule types and at least one of the one or more cell types in one or more spatially-discrete portions of the quasi-planar substrate.

30. The system of claim 1, wherein the controller is configured to direct motion of at least one of the one or more laterally-mobile effector molecule types toward or away from at least one of the one or more cell types.

31. The system of claim 1, wherein the controller is configured to respond by introducing one or more components into or onto at least one of the one or more cell types.

32. The system of claim 1, wherein the controller is configured to respond by applying fluidic force or motional force to the one or more laterally-mobile effector molecule types or the quasi-planar substrate.

33. The system of claim 32, wherein force is transferred to the cell by one or more bound laterally-mobile effector molecule types.

34. The system of claim 1, wherein the controller is configured to respond by applying motional force to the one or more cell types.

35. The system of claim 1, wherein the controller is configured to respond by altering connectivity of the quasi-planar substrate.

36. The system of claim 1, wherein the controller is configured to move at least one of the one or more cell types between one or more spatially discrete portions of the quasi-planar substrate.

37. The system of claim 1, wherein the controller is configured to rotate at least one of the one or more cell types to a new orientation.

38. The system of claim 1, wherein the controller is configured to rotate at least one of the one or more cell types by differential binding or release at one or more different sites on the at least one of the one or more cell types.

39. The system of claim 1, wherein the controller is configured to expose different cell regions or cell receptors to the quasi-planar substrate.

40. The system of claim 1, wherein the controller is configured to respond to binding of at least one of the one or more cell types at one region of the quasi-planar substrate by altering a configuration of the two or more laterally-mobile effector molecule types at a second region on the quasi-planar substrate.

41. A system comprising
one or more fluid bypasses configured to receive and process at least one of the one or more cell types in one or more fluids from a vertebrate subject through a device and configured to return processed fluids or cells through the one or more fluid bypasses into the vertebrate subject;
wherein the device includes a quasi-planar substrate; and two or more laterally-mobile effector molecule types at least partially embedded within the quasi-planar substrate, wherein the two or more laterally-mobile effector molecule types are sequentially placed and configured to interact with one or more cell types;
one or more cell bays including one or more sensors configured to detect at least one of binding between the two or more laterally-mobile effector molecule types and the one or more cell types, cell bay occupancy, protein expression, or cell product secretion; and
at least one controller in communication with the one or more sensors, wherein the at least one controller is configured to responsively initiate modification of at least one of the two or more laterally-mobile effector molecule types, the quasi-planar substrate, or the one or more cell types, provide cytokines, or cause microfluidic flow in the cell bay to wash the cell or to move the cell to a new location.

42. The system of claim 41, wherein the one or more cell types include lymphocytes.

43. The system of claim 41, wherein the one or more cell types include T cells.

44. The system of claim 41, wherein the two or more laterally-mobile effector molecules include cancer antigens.

45. The system of claim 41, wherein the fluid includes blood or fractionated blood.

46. The system of claim 41, wherein the one or more cell bays are coated with at least one of a cytokine, a lipid bilayer, or one or more antibodies.

* * * * *